(12) United States Patent
Zoll et al.

(10) Patent No.: US 9,974,638 B2
(45) Date of Patent: May 22, 2018

(54) DEVICES AND METHODS FOR DELIVERY OF IMPLANTS

(71) Applicant: Boston Scientific Scimed, Inc., Maple Grove, MN (US)

(72) Inventors: Jonathan Zoll, Brookline, MA (US); Peter J. Pereira, Mendon, MA (US); Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 202 days.

(21) Appl. No.: 14/718,970

(22) Filed: May 21, 2015

(65) Prior Publication Data
US 2015/0351888 A1   Dec. 10, 2015

Related U.S. Application Data

(60) Provisional application No. 62/007,586, filed on Jun. 4, 2014.

(51) Int. Cl.
| | |
|---|---|
| *A61F 2/00* | (2006.01) |
| *A61B 17/00* | (2006.01) |
| *A61B 17/06* | (2006.01) |
| *A61B 50/30* | (2016.01) |

(52) U.S. Cl.
CPC ...... *A61F 2/0045* (2013.01); *A61B 17/00234* (2013.01); *A61B 17/06109* (2013.01); *A61B 50/30* (2016.02); *A61B 2017/00336* (2013.01)

(58) Field of Classification Search
CPC .... A61F 2/0031; A61F 2/0036; A61F 2/0045; A61F 2/92; A61F 2/93; A61F 2/95; A61F 2/962; A61F 2/966; A61F 2002/9517; A61F 2002/9522; A61B 17/00234; A61B 17/06109; A61B 2017/00292; A61B 2017/00336
See application file for complete search history.

(56) References Cited

U.S. PATENT DOCUMENTS

| 4,665,918 | A | * | 5/1987 | Garza | A61F 2/88 606/108 |
|---|---|---|---|---|---|
| 5,147,370 | A | * | 9/1992 | McNamara | A61F 2/88 606/108 |
| 5,147,387 | A | * | 9/1992 | Jansen | A61B 17/00234 606/108 |
| 5,201,757 | A | * | 4/1993 | Heyn | A61F 2/95 606/198 |

(Continued)

*Primary Examiner* — Ryan J Severson
(74) *Attorney, Agent, or Firm* — Brake Hughes Bellermann LLP

(57) ABSTRACT

According to an aspect, a medical device may include an elongated shaft configured to rotate about its longitudinal axis. The elongated shaft may include a retaining area configured to retain an implant. The medical device may include a sheath disposed around a portion of the elongated shaft. The elongated shaft may be configured to move in relation to the sheath. The elongated shaft may be configured to move in a direction parallel to the longitudinal axis between a first position and a second position. When the elongated shaft is in the first position, the retaining area is disposed outside of a cavity defined by the sheath. When the elongated shaft is in the second position, the retaining area is disposed within the cavity defined by the sheath.

17 Claims, 14 Drawing Sheets

(56) References Cited

U.S. PATENT DOCUMENTS

| | | | |
|---|---|---|---|
| 5,304,187 A | 4/1994 | Green et al. | |
| 5,387,235 A * | 2/1995 | Chuter | A61B 17/0469 606/194 |
| 5,464,403 A * | 11/1995 | Kieturakis | A61F 2/0063 128/898 |
| 5,503,623 A * | 4/1996 | Tilton, Jr. | A61B 17/00234 604/11 |
| 5,514,158 A * | 5/1996 | Kanesaka | A61B 17/0057 604/11 |
| 5,700,286 A * | 12/1997 | Tartaglia | A61F 2/07 604/104 |
| 5,766,157 A * | 6/1998 | Tilton, Jr. | A61B 17/00234 604/13 |
| 5,797,899 A * | 8/1998 | Tilton, Jr. | A61B 17/00234 604/181 |
| 5,824,053 A * | 10/1998 | Khosravi | A61F 2/88 606/195 |
| 5,833,707 A * | 11/1998 | McIntyre | A61F 2/92 606/108 |
| 5,919,184 A * | 7/1999 | Tilton, Jr. | A61B 17/00234 604/11 |
| 5,957,929 A * | 9/1999 | Brenneman | A61F 2/92 606/1 |
| 5,957,939 A * | 9/1999 | Heaven | A61B 17/00234 606/151 |
| 6,007,573 A * | 12/1999 | Wallace | A61B 17/12118 606/194 |
| 6,090,136 A * | 7/2000 | McDonald | A61F 2/07 623/1.23 |
| 6,090,996 A * | 7/2000 | Li | A61L 31/044 606/151 |
| 6,120,535 A * | 9/2000 | McDonald | A61F 2/92 623/1.39 |
| 6,156,045 A * | 12/2000 | Ulbrich | A61B 17/00234 604/158 |
| 6,187,015 B1 * | 2/2001 | Brenneman | A61F 2/92 606/108 |
| 6,193,731 B1 * | 2/2001 | Oppelt | A61B 17/00234 604/13 |
| 6,406,487 B2 * | 6/2002 | Brenneman | A61F 2/92 623/1.11 |
| 6,416,506 B1 * | 7/2002 | Tilton, Jr. | A61B 17/00234 606/1 |
| 6,425,915 B1 * | 7/2002 | Khosravi | A61F 2/88 623/1.11 |
| 6,478,803 B1 * | 11/2002 | Kapec | A61B 17/00234 606/151 |
| 7,011,674 B2 * | 3/2006 | Brenneman | A61F 2/92 606/108 |
| 7,364,541 B2 * | 4/2008 | Chu | A61B 17/00234 600/30 |
| 7,628,751 B2 * | 12/2009 | Bouffier | A61B 17/0401 600/30 |
| 7,651,519 B2 * | 1/2010 | Dittman | A61F 2/95 623/1.11 |
| 7,713,187 B2 * | 5/2010 | Chu | A61B 17/06109 600/30 |
| 7,846,171 B2 * | 12/2010 | Kullas | A61F 2/0063 604/15 |
| 7,867,222 B1 * | 1/2011 | Tilton, Jr. | A61B 17/00234 606/1 |
| 8,167,786 B2 * | 5/2012 | Chu | A61B 17/06109 600/30 |
| 8,221,440 B2 * | 7/2012 | Kullas | A61F 2/0063 604/15 |
| 8,317,808 B2 * | 11/2012 | Levin | A61F 2/0063 606/151 |
| 8,602,965 B2 * | 12/2013 | Chu | A61B 17/0469 600/37 |
| 8,734,319 B2 * | 5/2014 | Hanes, II | A61B 17/0218 600/37 |
| 8,734,473 B2 * | 5/2014 | Levin | A61F 2/0063 606/151 |
| 8,915,927 B2 * | 12/2014 | Chu | A61B 17/00234 606/139 |
| 8,920,483 B2 * | 12/2014 | Swanick | A61F 2/0063 606/151 |
| 8,951,185 B2 * | 2/2015 | Ogdahl | A61B 17/0401 600/37 |
| 9,050,164 B2 * | 6/2015 | Chu | A61B 17/06109 |
| 9,061,464 B2 * | 6/2015 | Li | A61F 2/04 |
| 9,149,261 B2 * | 10/2015 | Chu | A61B 17/00234 |
| 9,572,580 B2 * | 2/2017 | Sargeant | A61F 15/002 |
| 2001/0005793 A1 * | 6/2001 | Brenneman | A61F 2/92 623/1.11 |
| 2002/0151954 A1 * | 10/2002 | Brenneman | A61F 2/92 623/1.11 |
| 2004/0087970 A1 * | 5/2004 | Chu | A61B 17/00234 606/119 |
| 2005/0021128 A1 * | 1/2005 | Nakahama | A61F 2/92 623/1.15 |
| 2005/0075660 A1 * | 4/2005 | Chu | A61B 17/06109 606/190 |
| 2005/0107805 A1 | 5/2005 | Bouffier et al. | |
| 2005/0131391 A1 * | 6/2005 | Chu | A61B 17/00234 606/1 |
| 2005/0131392 A1 * | 6/2005 | Chu | A61B 17/00234 606/1 |
| 2005/0131393 A1 * | 6/2005 | Chu | A61B 17/00234 606/1 |
| 2006/0281966 A1 * | 12/2006 | Peacock, III | A61B 17/12 600/37 |
| 2007/0112361 A1 * | 5/2007 | Schonholz | A61B 17/00234 606/151 |
| 2008/0139877 A1 * | 6/2008 | Chu | A61B 17/0469 600/30 |
| 2008/0207988 A1 | 8/2008 | Hanes | |
| 2009/0234376 A1 | 9/2009 | Soltz et al. | |
| 2010/0055149 A1 * | 3/2010 | Li | A61F 2/04 424/425 |
| 2012/0215059 A1 * | 8/2012 | Chu | A61B 17/06109 600/30 |
| 2014/0249614 A1 * | 9/2014 | Levi | A61B 17/12022 623/1.11 |
| 2015/0216647 A1 * | 8/2015 | Chu | A61B 17/06109 600/30 |
| 2015/0351888 A1 * | 12/2015 | Zoll | A61F 2/0045 606/151 |
| 2016/0022401 A1 * | 1/2016 | Chu | A61B 17/00234 600/30 |

\* cited by examiner

DEVICES AND METHODS FOR DELIVERY OF IMPLANTS

CROSS-REFERENCE TO RELATED APPLICATION

This application is a Nonprovisional of, and claims priority to, U.S. Patent Application No. 62/007,586, filed on Jun. 4, 2014, entitled "DEVICES AND METHODS FOR DELIVERY OF IMPLANTS", which is incorporated by reference herein in its entirety.

TECHNICAL FIELD

This disclosure relates generally to medical devices and surgical procedures, and particularly medical devices and methods used for delivering implants.

BACKGROUND

Pelvic organ prolapse is an abnormal descent or herniation of the pelvic organs. A prolapse may occur when muscles and tissues in the pelvic region become weak and can no longer hold the pelvic organs in place correctly. Treatment for symptoms of the pelvic organ prolapse can include changes in diet, weigh control, and lifestyle. Treatment may also include surgery, medications, and the use of implants (e.g., graphs) to support the pelvic organs. Sacralcolpopexy is a surgical technique that may be used to repair pelvic organ prolapse. Sacralcolpopexy may be performed using an open abdominal technique or with the use of minimally invasive surgery, such as laparoscopy or robotic-assisted surgery. The sacralcolpopexy technique may use an implant to be inserted into the body. The implant may be attached to the anterior vaginal wall, the posterior vaginal wall, and the sacral promontory with the use of a coupling member such as a suture.

Delivery of the implant may require the implant to be rolled up before the implant can be introduced to the body. In some conventional approaches, the user may manually unroll the implant while the implant is inside the body. Furthermore, in cases where the implant is coated with a tacky substance, the delivery process may be relatively complicated.

SUMMARY

According to an aspect, a medical device may include an elongated shaft having a longitudinal axis. The elongated shaft may be configured to rotate about the longitudinal axis. The elongated shaft may include a retaining area configured to retain an implant in a rolled configuration such that the implant is wound around the elongated shaft at the retaining area. The medical device may include a sheath disposed around a portion of the elongated shaft. The elongated shaft may be configured to move in relation to the sheath. The elongated shaft may be configured to move in a direction parallel to the longitudinal axis between a first position and a second position. When the elongated shaft is in the first position, the retaining area is disposed outside of a cavity defined by the sheath. When the elongated shaft is in the second position, the retaining area is disposed within the cavity defined by the sheath.

The medical device may include one or more of the following features (or any combination thereof). The retaining area may include a slot. The slot may be configured to receive a portion of the implant. The slot may define an opening on a surface of the elongated shaft at the retaining area. The slot may include a first edge and a second edge such that the portion of the implant is received between the first edge and the second edge. The retaining area may include at least one protrusion on a surface of the elongated shaft. The elongated shaft may include a distal end portion. The distal end portion may be configured to engage the sheath when the elongated shaft is in the second position such that the cavity of the sheath and the distal end portion enclose the retaining area. The distal end portion may include a tissue piercing portion configured to pierce bodily tissue when inserted into a body of a patient. The tissue piercing portion may be blunt. The medical device may include at least one stopper member disposed on a portion of the elongated shaft. The at least one stopper member may be configured to substantially prevent movement in at least one direction of the elongated shaft. The stopper member may include a ring disposed around the portion of the elongated shaft. The sheath may include a protective portion and an extension portion. The retaining area may be disposed within a cavity defined by the protective portion when the elongated shaft is in the second position. The protective portion may have a size larger than the extension portion. The distal end portion of the elongated shaft may include an inner diameter portion and an outer diameter portion. The inner diameter portion may be disposed within a portion of the sheath such that inner diameter portion forms a cap closing an opening of the cavity of the sheath.

According to an aspect, a method for delivering an implant may include coupling an implant to a delivery device. The delivery device may include an elongated shaft and a sheath disposed around a portion of the elongated shaft. The sheath may define a cavity. The elongated shaft may include a distal end portion and a retaining area. The implant may be coupled to the retaining area. The method may include moving the elongated shaft relative to the sheath such that distal end portion engages the sheath. The cavity of the sheath and the distal end portion may form an enclosure. The implant may be disposed within the enclosure.

The method may include one or more of the following features (or any combination thereof). The retaining area may define a slot. The coupling the implant to the delivery device may include inserting a portion of the implant into the slot and rotating the elongated shaft such that the implant is wound around a surface of the retaining area. The method may include moving the elongated shaft relative to the sheath such that the implant is outside the cavity defined by the sheath, decoupling the implant from the delivery device. The decoupling the implant from the delivery device may include rotating the elongated shaft such that the implant is unwound from the retaining area.

According to an aspect, a medical device may include an elongated shaft having a longitudinal axis. The elongated shaft may be configured to rotate about the longitudinal axis. The elongated shaft may include a retaining area configured to retain an implant in a rolled configuration such that the implant is wound around the elongated shaft at the retaining area. The elongated shaft may include a sheath disposed around a portion of the elongated shaft. The elongated shaft may be configured to move in relation to the sheath. The elongated shaft may be configured to move in a direction parallel to the longitudinal axis between a first position and a second position. When the elongated shaft is in the first position, the retaining area is disposed outside of a cavity defined by the sheath. When the elongated shaft is in the second position, the retaining area is disposed within the cavity defined by the sheath.

The medical device may include one or more of the following features (or any combination thereof). The retaining area may include a slot. The slot may be configured to receive a portion of the implant. The retaining area may include at least one protrusion on a surface of the elongated shaft. The elongated shaft may include a distal end portion. The distal end portion of the elongated shaft may be configured to engage the sheath when the elongated shaft is in the second position such that the cavity of the sheath and the distal end portion enclose the retaining area. The distal end portion of the elongated shaft may include a tissue piercing portion configured to pierce bodily tissue when inserted into a body of a patient. The medical device may include at least one stopper member disposed on a portion of the elongated shaft. The at least one stopper member may be configured to substantially prevent movement in at least one direction of the elongated shaft. The stopper member may include a ring disposed around the portion of the elongated shaft. The sheath may include a protective portion and an extension portion. The retaining area may be disposed within a cavity defined by the protective portion when the elongated shaft is in the second position. The protective portion may have a size larger than the extension portion.

According to an aspect, a medical package may include an implant, and an elongated shaft having a longitudinal axis. The elongated shaft may be configured to rotate about the longitudinal axis. The elongated shaft may include a distal end portion and a proximal end portion. The distal end portion may include a tissue piercing portion. The elongated shaft may include a retaining area disposed between the distal end portion and the proximal end portion. The retaining area may be configured to retain the implant. The medical package may include a sheath disposed around a portion of the elongated shaft. The elongated shaft may be configured to move in relation to the sheath. The elongated shaft may be configured to move in a direction parallel to the longitudinal axis between a first position and a second position. When the elongated shaft is in the first position, the retaining area is disposed outside a cavity defined by the sheath. When the elongated shaft is in the second position, the distal end portion engages the sheath such that the implant is enclosed by the distal end portion and the cavity of the sheath.

The medical package may include one or more of the following features (or any combination thereof). The distal end portion of the elongated shaft may include an inner diameter portion and an outer diameter portion. The inner diameter portion may be disposed within a portion of the sheath such that inner diameter portion forms a cap closing an opening of the cavity of the sheath. The sheath may include a protective portion and an extension portion, the protective portion configured to be engaged with the distal end portion of the elongated shaft, the extension portion having a shape smaller than a shape of the protective portion. The retaining area may define a slot configured to receive a portion of the implant. The slot may define an opening on a surface of the elongated shaft at the retaining area. The slot may include a first edge and a second edge such that the portion of the implant is received between the first edge and the second edge. The tissue piercing portion may be blunt. The medical package may include a first stopper member configured to substantially prevent movement of the elongated shaft beyond the first position in a first direction, and a second stopper member configured to substantially prevent movement of the elongated shaft beyond the second position in a second direction. At least one of the first stopper member and the second stopper member may include a ring disposed around the portion of the elongated shaft.

According to an aspect, a method for inserting a delivery device may include coupling an implant to a delivery device. The delivery device may include an elongated shaft and a sheath disposed around a portion of the elongated shaft. The sheath may define a cavity. The elongated shaft may include a distal end portion and a retaining area. The implant may be coupled to the retaining area. The method may include moving the elongated shaft relative to the sheath such that distal end portion engages the sheath. The cavity of the sheath and the distal end portion may form an enclosure. The implant may be disposed within the enclosure.

The method may include one or more of the following features (or any combination thereof). The retaining area may define a slot. The coupling the implant to the delivery device may include inserting a portion of the implant into the slot and rotating the elongated shaft such that the implant is wound around a surface of the retaining area. The method may include moving the elongated shaft relative to the sheath such that the implant is outside the cavity defined by the sheath, and decoupling the implant from the delivery device. The decoupling the implant from the delivery device may include rotating the elongated shaft such that the implant is unwound from the retaining area.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are to medical devices, methods of making medical devices, and procedures for placing medical devices within a body of a patient. The term patient may hereafter be used for a person who benefits from the medical device or the methods disclosed in the present application. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1A:
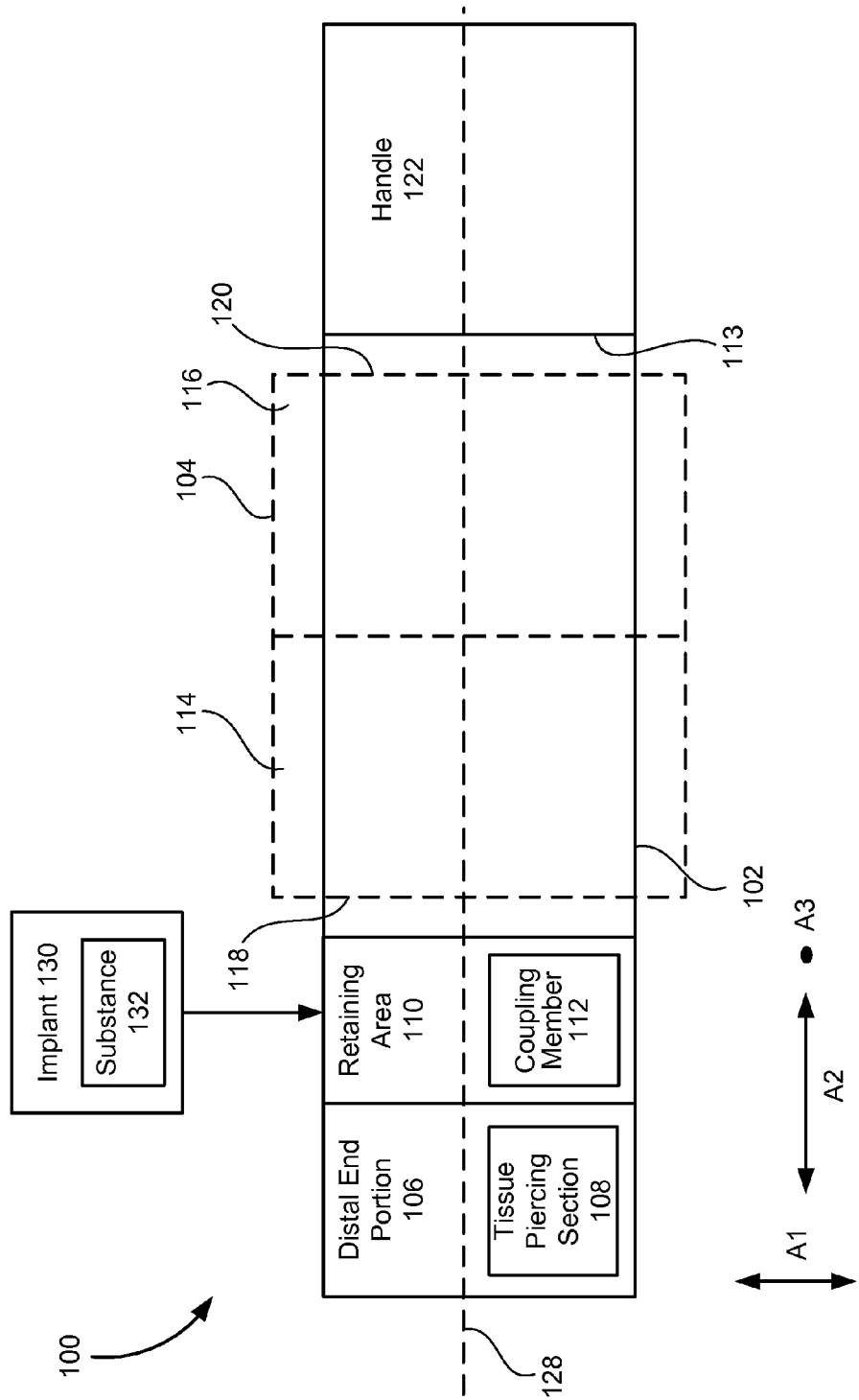
FIG. 1A illustrates diagram of a medical device for delivering an implant into a body of the patient within a first configuration according an aspect.
Figure 1B:
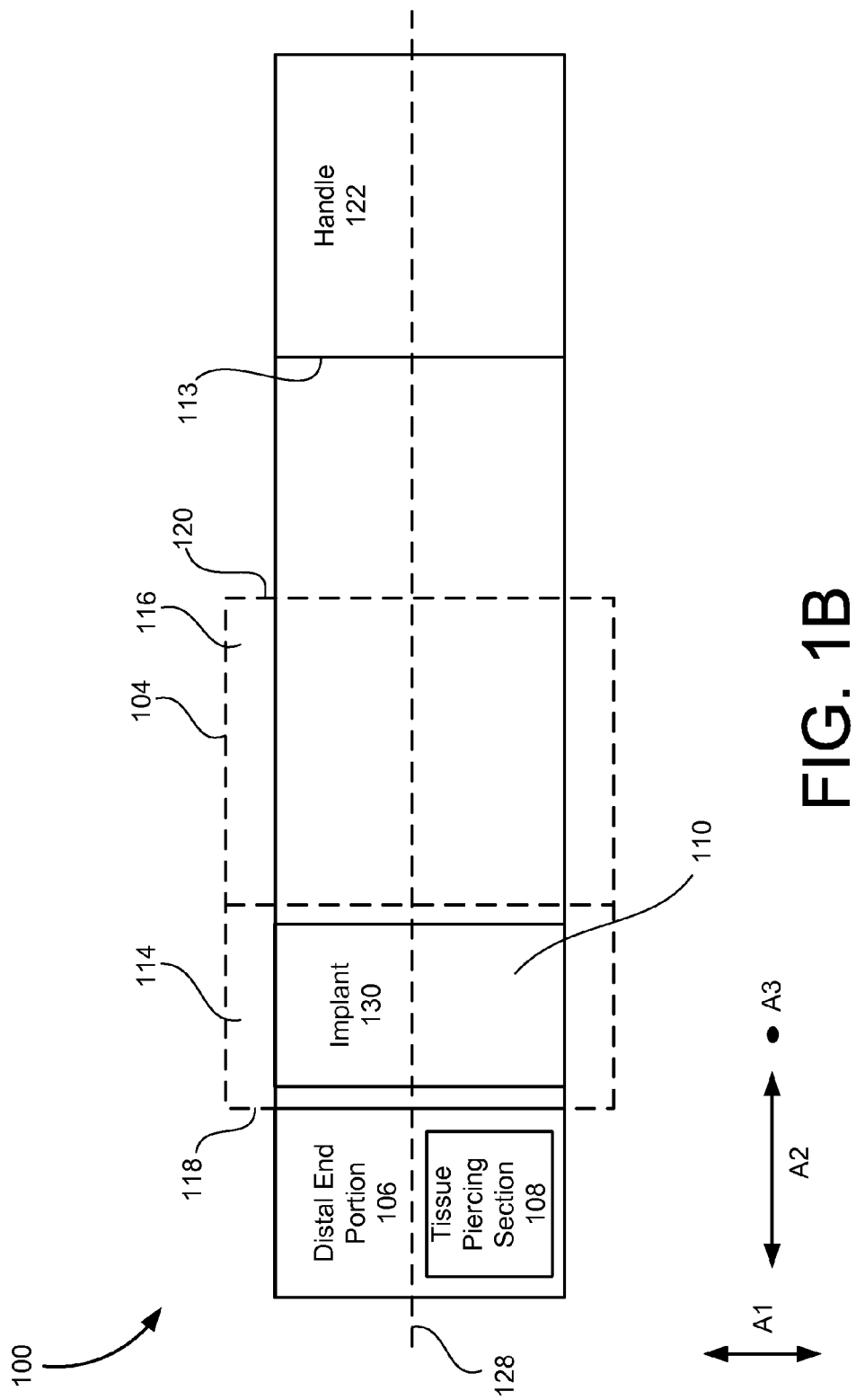
FIG. 1B illustrates diagram of a medical device for delivering an implant into a body of the patient within a second configuration according to an aspect.

FIGS. 1A and 1B are schematic diagrams of a medical device 100 configured to deliver an implant 130 into a body of the patient. The medical device 100 may be used to deliver the implant 130 into the body of the patient such that the implant 130 is protected during introduction into the body. Also, the medical device 100 may facilitate the coupling of the implant 130 in a rolled configuration before the medical device 100 is inserted into the body and the de-coupling of the implant 130 from the rolled configuration while the medical device 100 is in the body. The medical device 100 may be used for any type of procedure that places the implant 130 into the body of the patient. In some examples, the procedure may be a part in procedures such as a sacrocolpopexy. A sacralcolpopexy may be a surgical technique that may be used to repair pelvic organ prolapse. A sacralcolpopexy may be performed using an open abdominal technique or with the use of minimally invasive surgery, such as laparoscopy or robotic-assisted surgery. The medical device 100 may allow the operator to roll up the implant 130 so that the implant 130 can be delivered laparoscopically. Subsequently, the medical device 100 may unravel the implant 130 within the body so that the implant 130 can be secured. Also, the medical device 100 may be included as part of a package or kit that includes the implant 130. The package may further include a surgical instrument (e.g., vaginal manipulator), as well as potentially other types of components or instructions.

Referring to FIGS. 1A and 1B, the medical device 100 may be coupled to the implant 130, and the medical device 100 may be manipulated to enclose the implant 130 (e.g., moving from a first configuration shown in FIG. 1A to a second configuration shown in FIG. 1B). Then, the medical device 100 having the enclosed implant 130 may be inserted into the body of the patient until reaching a desired implantation location within the body. As such, the medical device 100 may prevent or help prevent the implant 130 from being exposed to the internal components of the body which may include various bodily fluids. Then, after the medical device 100 is inserted into the body, the medical device 100 may be manipulated to at least partially remove the enclosure from the implant 130, thereby exposing the implant 130 to the internal body environment (e.g., moving back to the first configuration shown in FIG. 1A from the second configuration shown in FIG. 1B). Then, the medical device 100 may be manipulated to de-couple the attached implant 130.

FIG. 1A illustrates the medical device 100 in the first configuration (e.g., a retracted, open, or exposed position). FIG. 1B illustrates the medical device 100 in the second configuration (e.g., an extended, closed, or protected position). For example, referring to FIGS. 1A and 1B, the medical device 100 may include an elongated shaft 102 having a central axis 128, a handle 122 coupled to the elongated shaft 102, and a sheath 104 disposed around a portion of the elongated shaft 102. In some examples, the elongated shaft 102 may be configured to rotate about the central axis 128 within the sheath 104 and/or the sheath 104 may be configured to rotate over the elongated shaft 102. Also, the elongated shaft 102 may be configured to move in directions along an axis A2 in relation to the sheath 104 (e.g., by pulling/pushing the handle 122 along the axis A2), thereby moving between the first and second configurations. The axis A2 may be parallel to the central axis of the 128 of the elongated shaft 102. An axis A1 may be perpendicular to the axis A2. An axis A3 into the page (shown as a dot) is orthogonal to the axes A1 and A2. The axes A1, A2, and A3 are used throughout several of the various views of the implementations described throughout the figures for simplicity.

Referring to FIG. 1A, the elongated shaft 102 may include a retaining area 110 configured to retain the implant 130 in a rolled configuration (e.g., where the implant 130 is wound around the elongated shaft 102 at the retaining area 110 based on the rotation of the elongated shaft 102). For example, a portion of the implant 130 may be placed on the retaining area 110, and then the elongated shaft 102 may be rotated, thereby winding the implant 130 around the elongated shaft 102 at the retaining area 110. In some examples, the handle 122 may be coupled to a proximate end portion 113 of the elongated shaft 102. As such, a user may grasp the handle 122 and rotate the handle 122, thereby causing the elongated shaft 102 to rotate.

The retaining area 110 may be a portion of the elongated shaft 102 that is configured to retain the implant 130. For example, the implant 130 may be coupled to the elongated shaft 102 at the retaining area 110. The retaining area 110 may be disposed between a distal end portion 106 of the elongated shaft 102 and the proximal end portion 113 of the elongated shaft 102. In some examples, the retaining area 110 is disposed adjacent to the distal end portion 106.

The retaining area 110 may include a coupling member 112. The coupling member 112 may be configured to couple a portion of the implant 130 to the retaining area 110. In some examples, the coupling member 112 may be a slot on the elongated shaft 102. In some examples, the slot may be an opening on the surface of the elongated shaft 102 such that a portion of the implant 130 may be inserted into the opening. In some examples, the slot may be defined by one or more portions of the elongated shaft 102. In some examples, the opening of the slot may be moveable. Then, the implant 130 may be wrapped around the elongated shaft 102 at the retaining area 110 by the rotation of the elongated shaft 102 such that the coupling member 112 may prevent or help prevent the implant 130 from slipping. In some examples, the coupling member 112 may be one or more protrusions on the elongated shaft 102. The protrusion(s) may engage a portion of the implant 130 such that the implant 130 may be prevented or substantially prevented from slipping as the elongated shaft 102 is rotated. In some examples, the coupling member 112 may be a portion of the elongated shaft 102 having an increased friction, or a material coupled to the elongated shaft 102 that provides an increased friction.

The elongated shaft 102 may be configured to move in relation to the sheath 104 along the axis A2 between the first configuration (as shown in FIG. 1A) and the second configuration (as shown in FIG. 1B), as well as any position between the first configuration and the second configuration. As shown in FIG. 1A, when the elongated shaft 102 is in the first configuration, the retaining area 110 is not disposed within the sheath 104. When in the first configuration, the implant 130 may be coupled to the elongated shaft 102 at the retaining area 110. Then, the elongated shaft 102 may move in a proximal direction along the axis A2 to the second configuration as shown in FIG. 1B. As shown in FIG. 1B, when the elongated shaft 102 is in the second configuration, the retaining area 110 is disposed within the sheath 104 thereby protecting the implant 130. Then, the medical device 100 may be inserted into the body into a desired location.

In some examples, the sheath 104 may include a distal end portion 118 and a proximal end portion 120. The distal end portion 118 may define a first opening. The proximal end portion 120 may define a second opening. A lumen may extend from the first opening to the second opening. In some examples, the second opening may be smaller than the first opening. The elongated shaft 102 may be disposed through the first and second openings. The sheath 104 may be a cylindrical structure having a diameter greater than a diameter of the elongated shaft 102. The sheath 104 may include a protective portion 114 and an extension portion 116. The protective portion 114 may be configured to be disposed over the retaining area 110 and engage the distal end portion 106 when in the second configuration. The extension portion 116 may be configured to be grasped by an operator. The protective portion 114 may be larger than the extension portion 116. The protective portion 114 may have a larger size than the implant 130 in the rolled configuration.

The distal end portion 106 may be a portion of the elongated shaft 102. In other examples, the distal end portion 106 may be a separate component that is coupled to the elongated shaft 102. In some examples, the distal end portion 106 may be considered a cap. The distal end portion 106 may include a different shape than the elongated shaft 102. Portions of the distal end portion 106 may be larger than the elongated shaft 102. The distal end portion 106 may have a structure configured to engage with the sheath 104. Also, when the distal end portion 106 is engaged with the sheath 104, the distal end portion 106 and the sheath 104 (or sheath portion thereof) form an enclosure over the retaining area 110 having the implant 130. In some examples, the retaining area 110 is fully or completely surrounded such that the implant 130 can be protected when the medical device 100 is inserted into the body. In some examples, the distal end portion 106 may have a structure that is used to form a fluid-tight (or water-tight) enclosure over the retaining area 110 such that the implant 130 can be protected when inserted into the body of the patient.

The distal end portion 106 may include a tissue piercing section 108. The tissue piercing section 108 may be configured to pierce bodily tissue as the medical device 100 is inserted into the body. The tissue piercing section 108 may be a blunt tip portion. In other examples, the tissue piercing section 108 may be a sharp tip portion.

The implant 130 may be a variety of shapes and sizes. In some examples, the implant 130 may be a Y-shaped implant. In some examples, the implant 130 may be circular, rectangular, square, curved, and/or a combination of one or more of these shapes. In some examples, the implant 130 may include extension members or arms that are used to couple the implant within the body of the patient.

The implant 130 may include a substance 132 such that the implant 130 may be considered tacky or sticky. As such, in the case of when the implant 130 includes the substance 132, the protection of the implant 130 by the medical device 100 from the bodily fluids is relatively important when inserting the implant 130 into the body. In other examples, the implant 130 may become tacky or sticky upon exposure to bodily fluids. The sheath 104 may protect the implant 130 from exposure to bodily fluids. The implant 130 may include a mesh material. The implant 130 may include a shape memory material such that when the implant 130 is exposed to heat inside the body, the implant 130 may unravel without the aid of an additional surgical instrument or other decoupling mechanisms. In this example, the sheath 104 may protect the implant 130 from the heat while the implant 130 is delivered into the body of the patient.

The implant 130 may include a film that may adhere to a surface of the implant 130. In this example, the implant 130 with the film may be rolled up without a surface of implant 130 making contact with itself. In the case where the implant 130 includes a tacky substance, the film may prevent or substantially prevent the implant 130 from sticking to itself. The film may be pulled off once the implant 130 is unraveled. In some examples, a tab may be coupled to the film to allow a surgical instrument to grab onto the tab to assist with pulling of the film.

In some examples, the implant 130 may include one or more loop portions. The loop portions may be formed by the material of the implant 130 or another material such as a suture. The loop portions may be grasped by a surgical instrument to aid in the unraveling. For example, once the rolled-up implant 130 is within the body, the operator may grasp one or more of the loop portions and unravel the implant 130. In some examples, the loop portions are disposed on opposite edge portions of the implant 130. In some examples, the loop portions may be disposed perpendicular (or diagonally) from the central axis 128. In other examples, the loop portions are disposed on side portions of the implant. In some examples, the loop portions are disposed on a similar orientation as the central axis 128. In some examples, the loop portions are disposed at set intervals to allow the operator to cut the implant 130 without hindering the ability to unravel the implant 130.

The elongated shaft 102 may be a cylindrical structure (e.g., tubular or circular structure). In some examples, the elongated shaft 102 may be a hollow cylindrical structure (e.g., defining a lumen along the central axis 128). In other examples, the elongated shaft 102 may be a solid structure (e.g., without a lumen). In some examples, the elongated shaft 102 may be considered a turning rod. The elongated shaft 102 may be straight or substantially straight along the central axis 128. In other examples, the elongated shaft 102 may include one or more curved portions. In some examples, the elongated shaft 102 (or a portion thereof) may be split into a first shaft and a second shaft. The elongated shaft 102 may be formed from a metal-based or polymer-based material.

Also, the elongated shaft 102 may include at least one stopper member configured to prevent movement or help prevent movement of the elongated shaft 102 in a distal direction and/or proximal direction along the axis A2. In some examples, the stopper member may be a ring (e.g., rubber, metal, or plastic ring) disposed around the elongated shaft 102. In other examples, the stopper member may be one or more protrusions on the surface of the elongated shaft 102. Also, the elongated shaft 102 may include a first stopper member configured to prevent distal movement or help prevent distal movement of the elongated shaft 102 in relation to the sheath 104 beyond a certain position, and a second stopper member configured to prevent proximal movement or help prevent proximal movement of the elongated shaft 102 in relation to the sheath 104 beyond a certain position. For example, the first and second stopper members may be disposed on the elongated shaft 102 such that the elongated shaft 102 is stopped from moving when pulled out or pushed in too far relative to the sheath 104. The second stopper member may be disposed a distance from the first stopper member. The distance between the first stopper member and the second stopper member may be equal or greater than the length of the retaining area 110 and/or the portion of the sheath 104 that covers the retaining area 110. The distance between the first stopper member and the second stopper member may correspond to the distance the elongated shaft 102 slides relative to the sheath 104.

Also, the medical device 100 may include an actuator configured to control the coupling member 112. For example, the actuator may facilitate the gripping or coupling of the portion of the implant 130 to the retaining area 110. If the coupling member 112 is a slot, the actuator may control the opening or closing of the slot. In some examples, the actuator may be a trigger, button, level, wire, thread, filament, and/or a combination of two or more of these components configured to control the coupling member 112. Also, the actuator may operate in conjunction with a motor included within the medical device 100. For example, the motor may drive the rotation of the elongated shaft 102 and/or the coupling member 112.

Figure 2A:
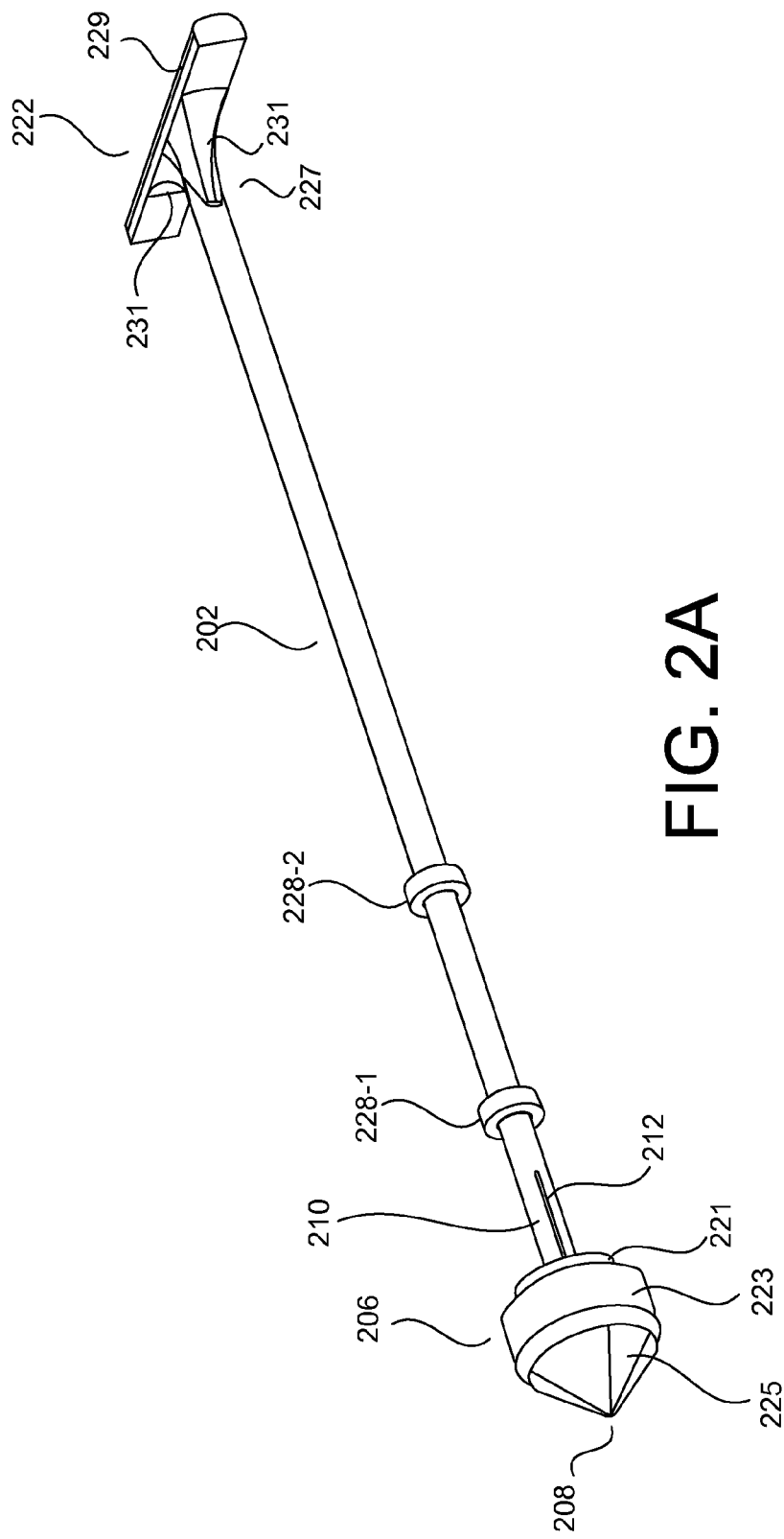
FIG. 2A illustrates an elongated shaft having a slot according to an aspect.
Figure 2B:
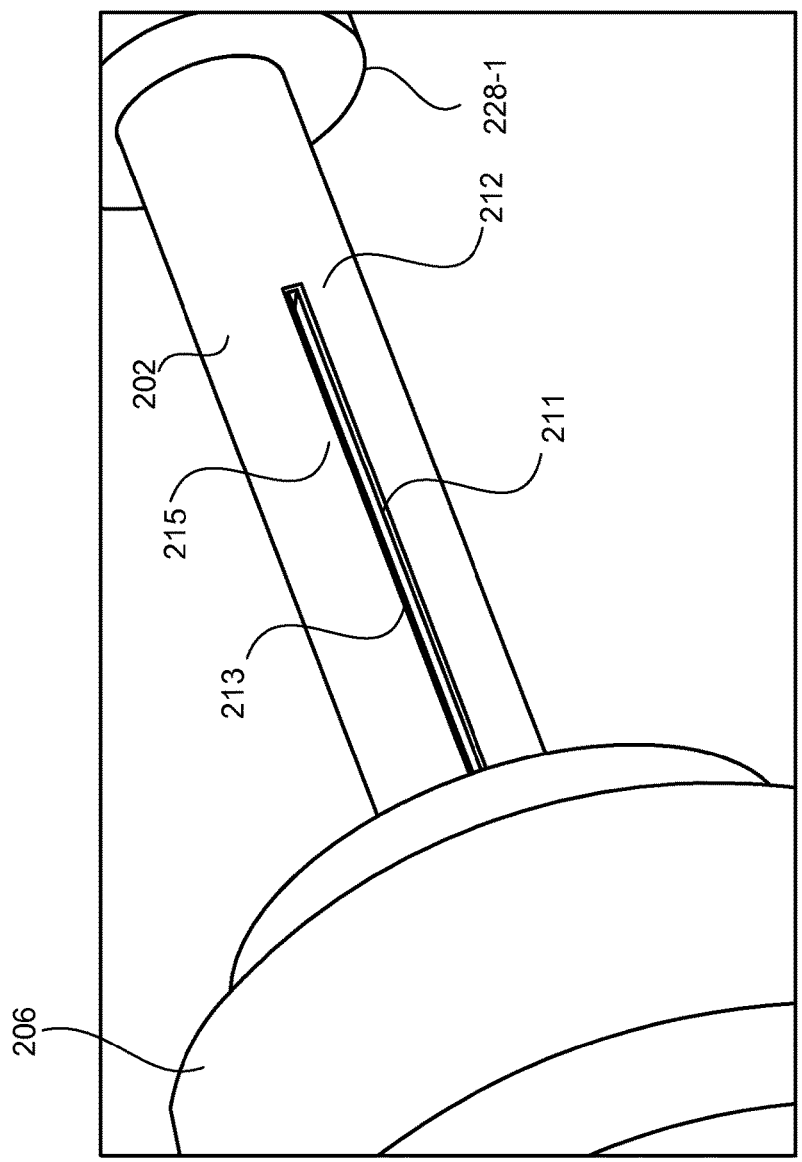
FIG. 2B illustrates a more detailed version of the slot of FIG. 2A according to an aspect.

FIGS. 2A and 2B illustrate example perspectives of an elongated shaft 202 according to an aspect. In some examples, the elongated shaft 202 of FIGS. 2A and 2B may be used in conjunction with the sheath of FIGS. 3A-3B. In some examples, the elongated shaft 202 of FIGS. 2A and 2B may be included as part of the medical devices described in FIGS. 4-5. Also, the elongated shaft 202 of FIGS. 2A-2B may be included as part of the medical device 100 of FIG. 1 or any other medical device described herein. FIG. 2A illustrate a perspective of the elongated shaft 202 having a slot 212 according to an aspect. FIG. 2B illustrate a more detailed version of the slot 212 of FIG. 2A according to an aspect.

Referring to FIGS. 2A-2B, the elongated shaft 202 may have a cylindrical structure that defines the slot 212 at the retaining area 210 of the elongated shaft 202. In some examples, the elongated shaft 202 may be a rod or other type of cylindrical or tubular structure. In other examples, the elongated shaft 202 may have a non-cylindrical structure. The elongated shaft 202 may include a distal end portion 206, and a handle 222 coupled to a proximal end portion 227 of the elongated shaft 202. Also, the elongated shaft may include a first stopper member 228-1 configured to prevent movement or help prevent of the elongated shaft 202 in relation to a sheath (e.g. the sheath 304 of FIGS. 3A-3B) in a first direction, and a second stopper member 228-2 configured to prevent or help prevent movement of the elongated shaft 202 in relation to the sheath in a second direction that is opposite to the first direction.

The elongated shaft 202 may be formed from a metal-based or polymer-based material. In some examples, the elongated shaft 202 may define a lumen. In some examples, the elongated shaft 202 may have one or more openings through the structure of the elongated shaft 202 that may be in communication with the lumen. In some examples, the structure of the elongated shaft 202 may define an inner diameter and an outer diameter (e.g. with a lumen). In some examples, the elongated shaft 202 may be a solid structure (e.g., without a lumen).

The slot 212 may be configured to receive a portion of an implant (e.g., the implant 130 discussed with reference to FIGS. 1A-1B). In some examples, the slot 212 may be configured to receive an edge portion (e.g., side portion, end portion, etc.) of the implant. Referring to FIG. 2B, the slot 212 may be an opening through a surface 215 (also referred to as a slit surface) of the elongated shaft 202. The slot 212 may be considered a cavity that extends into the elongated shaft 202. In some examples, the slot 212 may define a first edge 211 and a second edge 213, both of which extend into the structure of the elongated shaft 202. The first edge 211 may be adjacent to the second edge 213 such that the distance between the first edge 211 and the second edge 213 define the opening of the slot 212. The first edge 211 and the second edge 213 may be parallel to a longitudinal axis of the elongated shaft 202. In some examples, the slot 212 may be v-shaped or u-shaped.

Referring to FIGS. 2A and 2B, the size of the opening of the slot 212 may be slightly greater than a thickness of the portion of the implant to be inserted into the slot 212. However, in some examples, the size of the opening of the slot 212 may be small enough such that friction keeps or helps keep the portion of the implant inside the slot 212. The length of the slot 212 may be greater than the portion of the implant. The length of the slot 212 may be orientated such that the slot 212 is parallel with the longitudinal axis of the elongated shaft 202. The slot 212 may be disposed at any location on the elongated shaft 202 between the distal end portion 206 and the handle 222. In some examples, the slot 212 may be disposed proximate to the distal end portion 206.

For example, the slot 212 may be disposed close to the distal end portion 206 such that a relatively small distance exists between the distal end portion 206 and the distal end of the slot 212.

In some examples, the slot 212 may include one or more protrusions configured to grip the portion of the implant. For example, referring to FIG. 2B, the protrusions may be disposed within the slot 212, e.g., on the first edge 211 and/or the second edge 213. In other examples, the first edge 211 and/or the second edge 213 of the slot 212 may be formed with an increased friction to keep the portion of the implant within the slot 212. In other examples, the slot 212 at the surface 215 may include one or more protrusions (e.g., dimples) that are arranged and sized to fit into the openings of a mesh implant as the mesh implant is wrapped around the retaining area 210.

Referring to FIGS. 2A and 2B, the retaining area 210 may be a portion of the elongated shaft 202 that is configured to retain the implant. For example, the implant may be coupled to the elongated shaft 202 at the retaining area 210. The implant may be wrapped around the elongated shaft 202 at the retaining area 210. In some examples, the retaining area 210 may be the slot 212. The retaining area 210 may have a length greater than a length of the slot 212. In some examples, the retaining area 210 may be the outer surface of the portion of the elongated shaft 202 configured to engage the implant. In some examples, the retaining area 210 may be the slot 212 and the outer surface of the portion of the elongated shaft 202. The retaining area 210 may be disposed between the distal end portion 206 of the elongated shaft 202 and the proximal end portion 227 of the elongated shaft 202. The retaining area 210 may be disposed adjacent to the distal end portion 206. The retaining area 210 may be configured to retain the implant in a rolled configuration such that the implant is wound around the elongated shaft 202 at the retaining area 210 based on the rotation of the elongated shaft 202. Also, the implant may be decoupled at the retaining area 210 based on the rotation of the elongated shaft 202 in the opposite direction.

The handle 222 may have a structure that is configured to be grasped by the operator. The handle 222 may be coupled to the proximal end portion 227 of the elongated shaft 202. In some examples, the handle 222 may define a lumen in communication with the lumen of the elongated shaft 202. In some examples, the handle 222 may include one or more openings. The handle 222 may be rotated by the operator such that the elongated shaft 202 is rotated about its longitudinal axis in order to couple the implant around the elongated shaft 202 or de-couple the implant from the elongated shaft 202. Also, the handle 222 may be pushed or pulled in order to move the elongated shaft 202 relative to the sheath such that the sheath can cover the retaining area 210 (thereby enclosing the implant) or expose the retaining area 210 (thereby exposing the implant).

As shown in FIG. 2A, the handle 222 may be T-shaped. For example, the handle 222 may include a handle end portion 229 that extends in a direction perpendicular to the length of the elongated shaft 202, and handle side portions 231 that extend from the handle end portion 229 and overlap with the proximal end portion 227 of the elongated shaft 202. In other examples, the handle 222 may be an extension of the elongated shaft 202, e.g., including the same or similar structure. In other examples, the handle 222 may be a rounded structure (e.g., knob).

The distal end portion 206 may have a structure configured to engage with the sheath. In some examples, the distal end portion 206 may be considered a cap. In some examples, the distal end portion 206 is a separate component from the elongated shaft 202. In other examples, the distal end portion 206 and the elongated shaft 202 are unitarily formed. When the distal end portion 206 is engaged with the sheath, the distal end portion 206 and the sheath (or sheath portion thereof) form an enclosure over the retaining area 210 having the implant. In some examples, the retaining area 210 is fully or completely surrounded such that the implant can be protected when the medical device is inserted in to the body. In some examples, the distal end portion 206 may have a structure that is used to form a fluid-tight (or water-tight) enclosure over the retaining area 210 such that the implant can be protected when inserted into the body of the patient. Also, the distal end portion 206 may have a structure that is configured to pierce bodily tissue as the elongated shaft 202 is inserted into the body of the patient. The distal end portion 206 may have a cylindrical shape with at least one portion having a greater diameter than the other portions of the elongated shaft 202. The greater diameter portion of the distal end portion 206 may be configured to engage the sheath.

The distal end portion 206 may include an inner diameter portion 221, an outer diameter portion 223, and a tapered portion 225 that tapers to a tip portion 208. Each of the inner diameter portion 221, the outer diameter portion 223, and the tapered portion 225 may be cylindrical shaped of various sizes. The inner diameter portion 221 may have a diameter greater than a diameter of the elongated shaft 202. The diameter of the inner diameter portion 221 may be slightly smaller than an inner diameter of the sheath such that the inner diameter portion 221 can be disposed within an opening of the sheath.

The outer diameter portion 223 may have a diameter larger than the inner diameter portion 221. The portion of the distal end portion 206 between the inner diameter portion 221 and the outer diameter portion 223 may form an edge configured to engage a leading surface (e.g., leading cylindrical surface 341 of FIG. 3B) of the sheath. In some examples, the outer diameter portion 223 may have a diameter that substantially corresponds to the outer diameter of the sheath.

The tapered portion 225 may extend from the outer diameter portion 223 and tapper until reaching the tip portion 208. The diameter of the tapered portion 225 may gradually decrease in the direction towards the tip portion 208. The tapered portion 225 may have a cylindrical cone shape. The tip portion 208 may be configured to pierce bodily tissue as the tip portion 208 is inserted into the body of the patient. In some examples, the tip portion 208 may be sharp. In some examples, the tip portion 208 may be blunt or rounded.

The first stopper member 228-1 may be configured to prevent distal movement or help prevent distal movement of the elongated shaft 202 in relation to the sheath beyond a certain position. The second stopper member 228-2 may be configured to prevent proximal movement or help prevent proximal movement of the elongated shaft 202 in relation to the sheath beyond a certain position. For example, the first and second stopping members 228 may be disposed on the elongated shaft 202 such that the elongated shaft 202 is stopped from moving when pulled out or pushed in too far relative to the sheath. The second stopper member 228-2 may be disposed a distance from the first stopper member 228-1. The distance between the first stopper member 228-1 and the second stopper member 228-2 may be equal or greater than the length of the retaining area 210 and/or the portion of the sheath that covers the retaining area 210. The distance between the first stopper member 228-1 and the second stopper member 228-2 may correspond to the distance the elongated shaft 202 slides relative to the sheath. In some examples, the distance between the first stopper member 228-1 and the second stopper member 228-2 may be greater or smaller than the travel distance of the elongated shaft 202 relative to the sheath. The first stopper member 228-1 may be disposed proximate to the slot 212 such that a short distance exists between the first stopper member 228-1 and the end portion of the slot 212. The second stopper member 228-2 may be disposed proximally from the first stopper member 228-1.

As shown in FIG. 2A, the first stopper member 228-1 and/or the second stopper member 228-2 may be a ring disposed around a portion of the outer surface of the elongated shaft 202. The first stopper member 228-1 and/or the second stopper member 228-2 may be a plastic, rubber, and/or metal ring. The first stopper member 228-1 and/or the second stopper member 228-2 may have an outer diameter sufficient to engage a portion of the sheath to prevent or help further movement of the elongated shaft 202. The outer diameter of the first stopper member 228-1 and/or the second stopper member 228-2 may be larger than an opening (e.g., through-hole 336 in FIG. 3B) of the sheath. In other alternative examples, the first stopper member 228-1 and/or the second stopper member 228-2 may be one or more raised detents on the elongated shaft 202 such that the raised detects engage a portion of the sheath as the elongated shaft 202 is pulled in or pushed out. In other examples, the first stopper member 228-1 and/or the second stopper member 228-2 may be a portion of the elongated shaft 202 having an increased diameter.

Figure 3A:
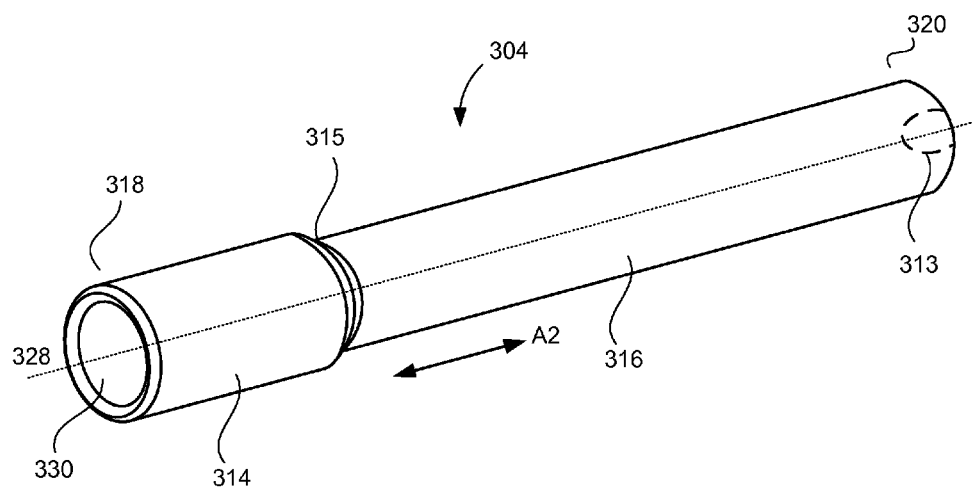
FIG. 3A illustrates a sheath according to an aspect.
Figure 3B:
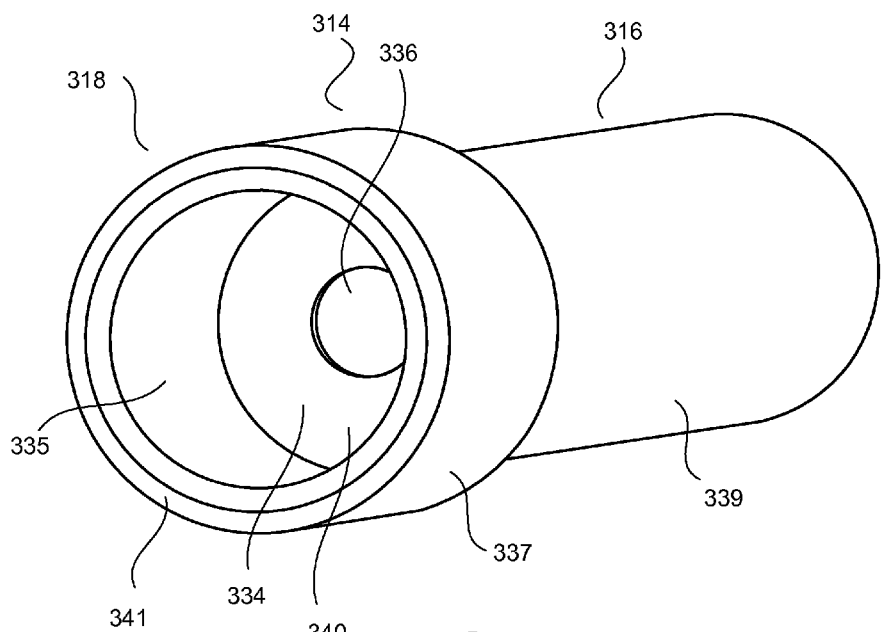
FIG. 3B illustrates a more detailed version of the sheath of FIG. 3A according to an aspect.

FIGS. 3A and 3B illustrate a sheath 304 according to an aspect. The sheath 304 of FIGS. 3A and 3B may be used in conjunction with the elongated shaft 202 of FIGS. 2A and 2B. For example, the sheath 304 may be disposed around a portion of the elongated shaft 202. Although the following description use the components of FIGS. 2A-2B, it is noted that the sheath 304 may also operate with any of the medical devices described herein such as the medical device 100 of FIGS. 1A-1B or any other figure described herein.

The structure of the sheath 304 may have a diameter larger than the elongated shaft 202 such the elongated shaft 202 is disposed within the sheath 304. In some examples, the sheath 304 may be configured to rotate about its central axis 328 with respect to the elongated shaft 202. The sheath 304 may include one or more inner diameters and one or more outer diameters. The length of the sheath 304 may be smaller than the length of the elongated shaft 202. The sheath 304 may be formed from a plastic, rubber, or polymer-based material. In some examples, the sheath 304 may have a cylindrical structure.

The sheath 304 may have a distal end portion 318 and a proximal end portion 320. The sheath 304 may define a lumen extending between the distal end portion 318 and the proximal end portion 320. As shown in FIG. 3A, the distal end portion 318 of the sheath 304 may define an opening 330 configured to receive the implant when placed over the retaining area 210. The opening 330 may have a size larger than the implant that is coupled to the retaining area 210. For example, if the implant is rolled around the elongated shaft 202 at the retaining area 210, the opening 330 may be larger than the rolled implant. The proximal end portion 320 may be configured to define an opening 313. The opening 313 may be smaller than the opening 330. In some examples, the opening 313 on the proximal end portion 320 may be slightly larger than the diameter of the elongated shaft 202 such that the elongated shaft 202 may slide and rotated within the opening 313. In other examples, the proximal end portion 320 does not have the opening 313 (e.g., the proximal end portion 320 includes a closed end).

The sheath 304 may include a protective portion 314, a tapered portion 315, and an extension portion 316. As shown in FIGS. 3A-3B, the protective portion 314 may define the opening 330. The extension portion 316 may define the opening 313. The protective portion 314 may be a cylindrical structure configured to be disposed over the retaining area 210 of the elongated shaft 202 when the sheath 304 engages the distal end portion 206 of the elongated shaft 202. The extension portion 316 may be a cylindrical structure configured to be disposed over the elongated shaft 202. The extension portion 316 may be grasped by the operator such that the sheath 304 remains relatively stationary when the elongated shaft 202 is moved. In other examples, the extension portion 316 may be grasped by the operator and moved relative the elongated shaft 202. The protective portion 314 and the extension portion 316 form a unitary shaft structure. In other examples, the protective portion 314 and the extension portion 316 are separate components that are coupled together.

The protective portion 314 may be larger than the extension portion 316. For example, the protective portion 314 may include an inner diameter defined by an inner surface 335 of the protective portion 314 and an outer diameter defined by an outer surface 337 of the protective portion 314. The extension portion 316 may include an inner diameter defined by an inner surface (not visible in FIGS. 3A-3B) and an outer diameter defined by an outer surface 339 of the extension portion 316. The inner diameter of the protective portion 314 may be larger than the inner diameter of the extension portion 316.

The tapered portion 315 may be disposed between the protective portion 314 and the extension portion 316. The tapered portion 315 may be a cylindrical structure having a diameter that decreases in the proximal direction. For example, the diameter of the tapered portion 315 may correspond to the outer diameter of the protective portion 314 and than taper until reaching the outer diameter of the extension portion 316.

The protective portion 314 may define a leading cylindrical surface 341. As the sheath 304 engages the distal end portion 206, the leading cylindrical surface 341 may be configured to engage the edge formed by the portion of the distal end portion 206 between the inner diameter portion 221 and the outer diameter portion 223.

The protective portion 314 may define a barrier portion 334 within the sheath 204. In some examples, the barrier portion 334 may be a circular member having a diameter. In some examples, the barrier portion 334 may be a ring member. The barrier portion 334 may be disposed on the proximal end of the protective portion 314 (e.g., opposite to the opening 330). The barrier portion 334 may define a through-hole 336. The through-hole 336 may be defined in the center of the barrier portion 334. The through-hole 336 may have a size slightly larger than the diameter of the elongated shaft 202 such that the elongated shaft 202 may slide and rotate within the through-hole 336. The through-hole 336 have a size such that the elongated shaft 202 may slide and rotate, but the elongated shaft 202 and the barrier portion 334 form a closed end such that fluids are prevented or substantially prevented from being transferred to the extension portion 316. The barrier portion 334 may be configured to form part of the enclosure that encloses the retaining area 210 when the sheath 304 is engaged with the distal end portion 206.

Figure 4A:
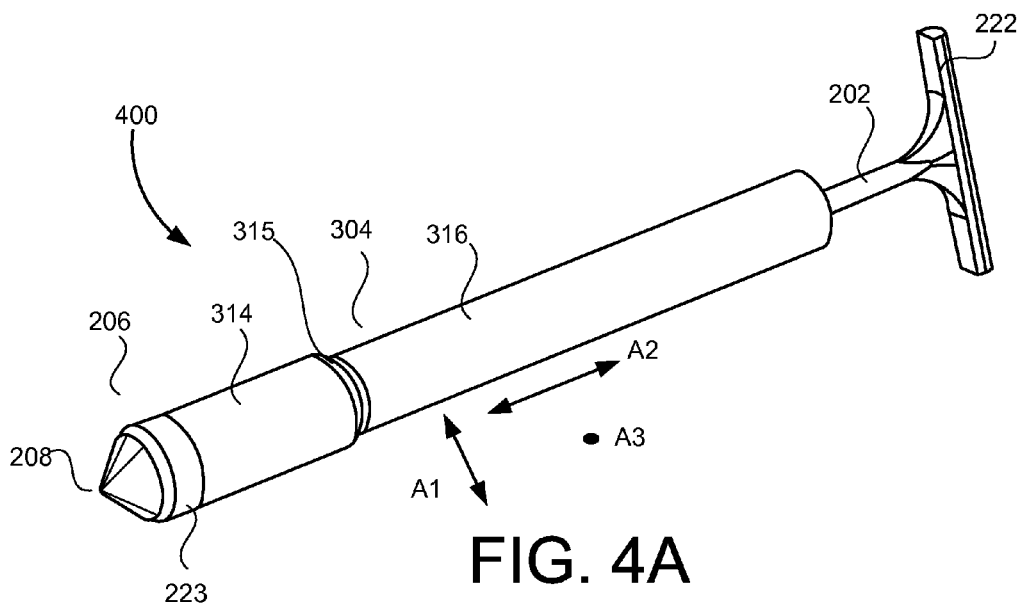
FIG. 4A illustrates a medical device having the elongated shaft and the sheath in a first configuration according to an aspect.
Figure 4B:
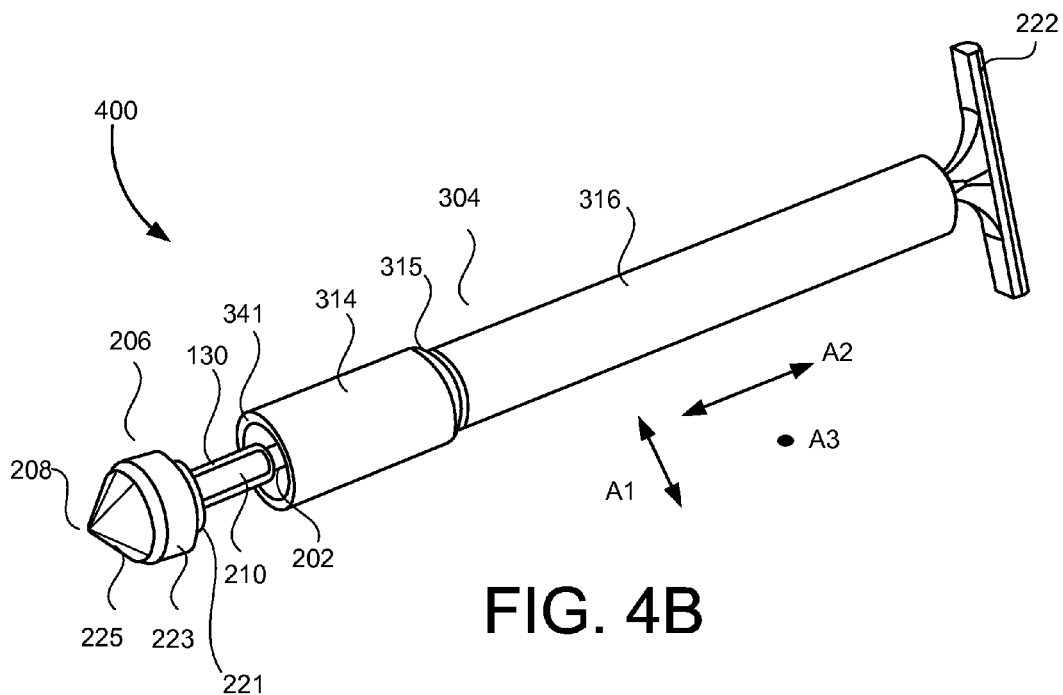
FIG. 4B illustrates the medical device of FIG. 4A in a second configuration according to an aspect.

FIG. 4A illustrate a medical device 400 having the elongated shaft 202 of FIGS. 2A-B and the sheath 304 of FIGS. 3A-B in a closed position according to an aspect. FIG. 4B illustrate the medical device 400 having the elongated shaft 202 of FIGS. 2A-B and the sheath of FIGS. 3A-3B in an open position according to an aspect.

Referring to FIGS. 4A-4B, the elongated shaft 202 may be configured to move relative to the sheath 304 along the axis A2 from the closed position as shown in FIG. 4A to the open position as shown in FIG. 4B (and vice versa). For example, an operator may grasp the handle 222 with one hand and grasp the extension portion 316 of the sheath 304. Then, the operator may push or pull the handle 222 while holding the sheath 304 stationary in order to move the elongated shaft 202 relative to the sheath 304. The movement of the elongated shaft 202 relative to the sheath 304 may be limited based on the stopping members 228 which are further shown and described with respect to FIGS. 5A-5B.

Referring to FIG. 4B, the medical device 400 is in the open position. For example, the elongated shaft 202 may be distally moved in relation to the sheath 304 along the axis A2, thereby exposing the retaining area 210 of the elongated shaft 202. In the open position, the implant 130 may be coupled to the retaining area 210 before inserting the medical device 400 in the body of the patient, or the implant 130 may be de-coupled from the retaining area 210 after reaching the desired location in the body.

Referring to FIG. 4A, the medical device 400 has been moved to the closed position. For example, the elongated shaft 202 is proximally moved in relation to the sheath 304 along the axis A2, thereby enclosing the retaining area 210 of the elongated shaft 202. In the closed position, the inner diameter portion 221 may be disposed within the protective portion 314 of the sheath 304. Also, in the closed position, the leading cylindrical surface 341 may be configured to engage the edge formed by the portion of the distal end portion 206 between the inner diameter portion 221 and the outer diameter portion 223.

The distal end portion 206 and the protective portion 314 of the sheath 304 may form an enclosure around the retaining area 210 having the implant 130 coupled thereto. In some examples, the enclosure may help keep bodily fluids from being exposed to the implant while the implant is inserted during the body of the patient. The distal end portion 206 and the protective portion 314 of the sheath 304 may fully enclose the retaining area 210 having the implant 130 coupled thereto. In particular, the inner diameter portion 221 may function as a first cap that closes one end of the protective portion 314 of the sheath 304. Also, the barrier portion 334 with the elongated shaft 202 being disposed through the through-hole 336 may function as a second cap that closes the other end of the protective portion 314 of the sheath 304. In other examples, instead of forming the enclosure with the distal end portion 206, the medical device 400 may include a removable cap that can be fitted on the opening 330 of the protective portion 314 in order to close that opening of the protective portion 314.

In some examples, the protective portion 314 of the sheath 304 may be filled with a gel substance such that when the implant 130 is drawn into the protective portion 314, the implant 130 is submerged and coated with the gel substance. The gel substance may be an antimicrobial or antibacterial coating. In some examples, the gel substance may be an adhesive. In some examples, the gel substance may be a therapeutic agent. The enclosure formed by the distal end portion 206 and the protective portion 314 of the sheath 304 forms a water-tight seal. In some examples, the gel substance may be injected through the distal end portion 106 or through a portion of the sheath 304 through a membrane.

Figure 5A:
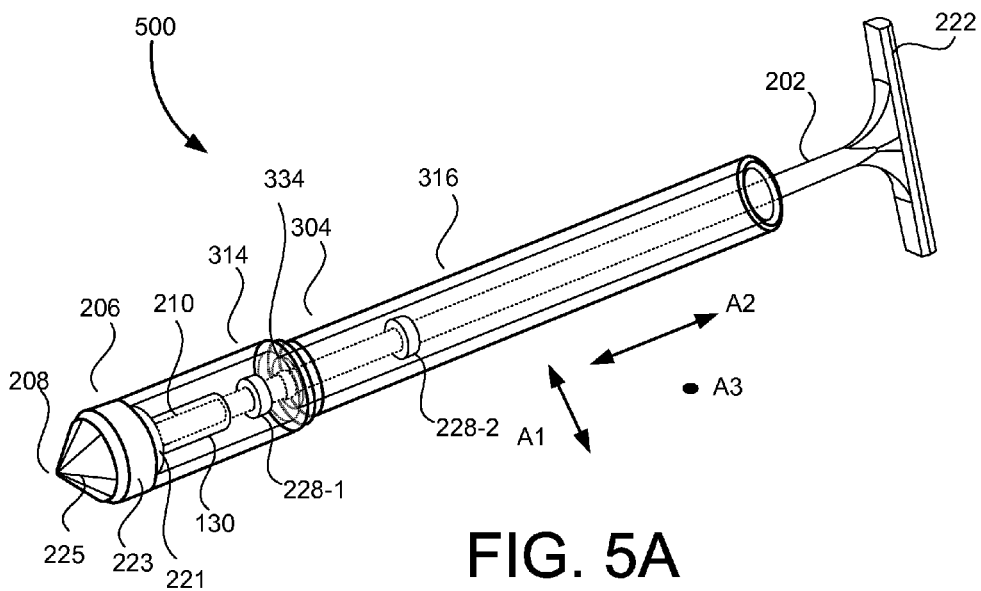
FIG. 5A illustrates the medical device having the elongated shaft and the sheath in a first configuration according to an aspect.
Figure 5B:
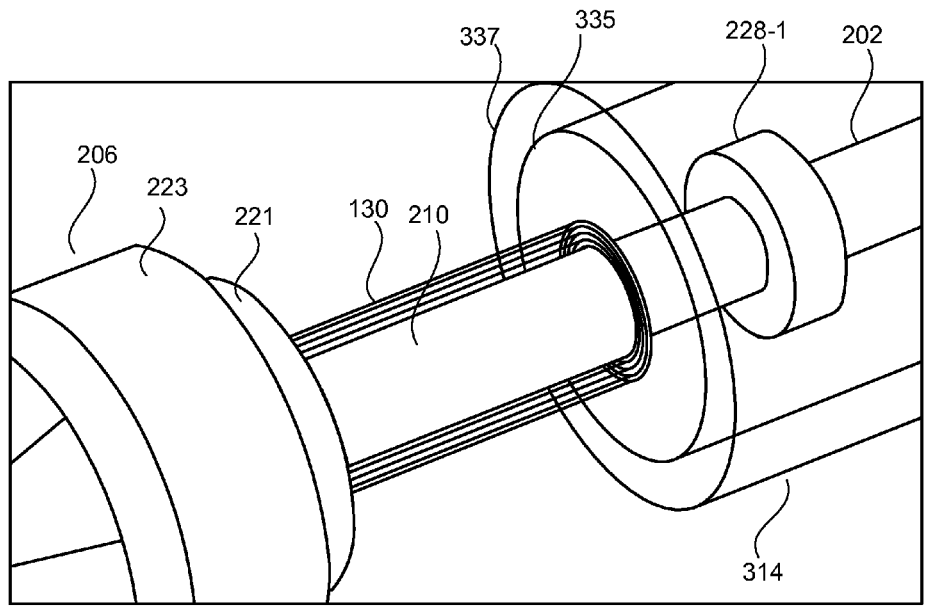
FIG. 5B illustrates the medical device of FIG. 5A in a second configuration according to an aspect.

FIG. 5A illustrates a medical device 500 having the elongated shaft 202 of FIGS. 2A-B and a see-through version of the sheath 304 of FIGS. 3A-B in the closed position according to an aspect. FIG. 5B illustrate a more detailed view of the medical device 500 of FIG. 5A in the open position according to an aspect.

As shown in FIGS. 5A-5B, the sheath 304 may be disposed around the elongated shaft 202. The elongated shaft 202 is coupled to the distal end portion 206 and the handle 222. In this example, the implant 130 is coupled to the elongated shaft 202 at the retaining area 210 such that the implant 130 is in the rolled configuration. Referring to FIG. 5A, the elongated shaft 202 has been moved in the proximal direction such that the protective portion 314 of the sheath 304 engages the distal end portion 206. Referring to FIG. 5B, the medical device 500 is in the open position. For example, the elongated shaft 202 is distally moved in relation to the sheath 304 along the axis A2, thereby exposing the retaining area 210 having the implant 130 coupled thereto.

As shown in FIG. 5A, the first stopper member 228-1 may be disposed on a distal side of the barrier portion 334, and the second stopper member 228-2 may be disposed on a proximal side of the barrier portion 334. Because the size of the first stopper member 228-1 is larger than the through-hole 336 of the barrier portion 334, the first stopper member 228-1 may be configured to prevent or help prevent the elongated shaft 202 from being pulled beyond the point of when the first stopper member 228-1 engages the barrier portion 334. Because the size of the second stopper member 228-2 is larger than the through-hole 336 of the barrier portion 334, the second stopper member 228-2 may be configured to prevent or help prevent the elongated shaft 202 from being pushed past the point of when the second stopper member 228-2 engages the barrier portion 334.

Figure 6A:
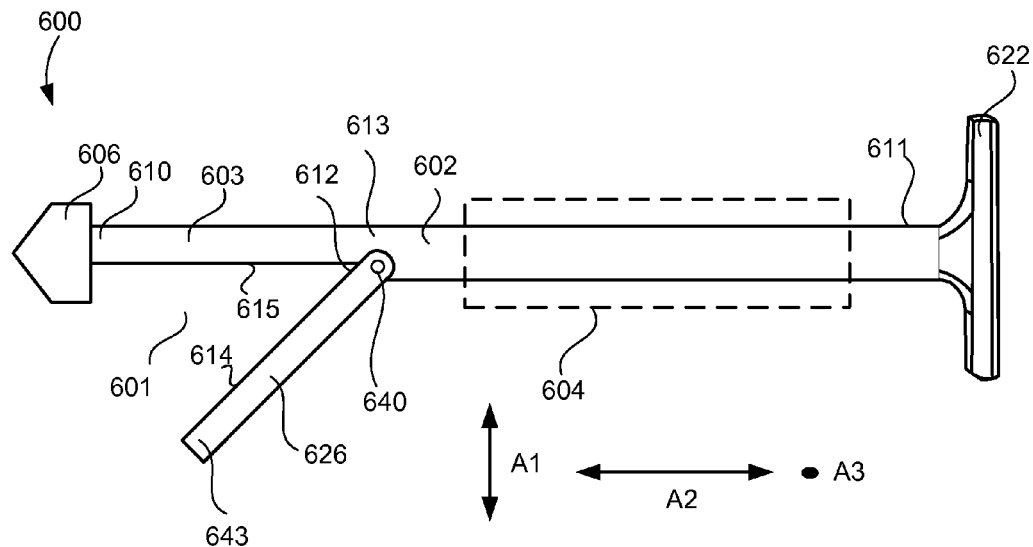
FIG. 6A illustrate a medical device in a first configuration according to another aspect.
Figure 6B:
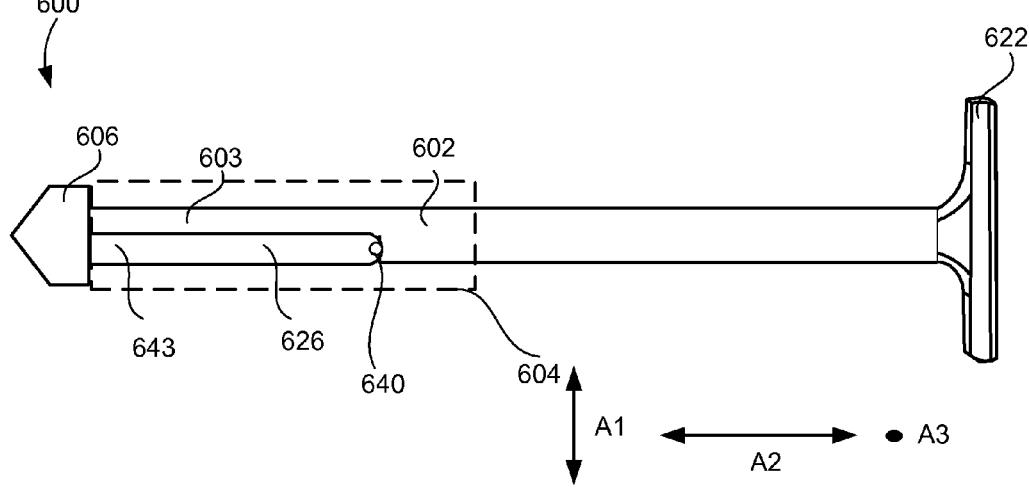
FIG. 6B illustrates the medical device of FIG. 6A in a second configuration according to an aspect.

FIGS. 6A and 6B illustrate perspectives a medical device 600 according to another aspect. The medical device 600 may include an elongated shaft 602, a cap 606 coupled to a distal end portion 610 of the elongated shaft 602, a handle 622 coupled to a proximal end portion 611 of the elongated shaft 602, and a sheath 604 disposed around a portion of the elongated shaft 602. In some examples, the cap 606 may be the distal end portion 106/206 of FIGS. 1-5, the handle 622 may be the handle 122/222 of FIGS. 1-5, the sheath 604 may be the sheath 104/204 of FIGS. 1-5, and the elongated shaft 602 may be the elongated shaft 102/202 of FIGS. 1-5. Because these components were previously described, the differences between the medical device 600 and the previous aspects will be discussed below. Also, the medical device 600 may include one or more stopping members 128/228 in order to limit the movement of the elongated shaft 602 in relation to the sheath 604.

Instead of using a slot 212 as shown in FIGS. 2A and 2B, the medical device 600 uses a type of clasping mechanism to grip the implant. In this aspect, the elongated shaft 602 is split into two portions (e.g., a central portion 603, a hinged portion 626) in order to create a slot 601. The central portion 603 may be an extension of the elongated shaft 602. As such, the cap 606 may be coupled to the distal end portion 610 of the central portion 603. The hinged portion 626 may be pivotally coupled to the central portion 603 via a hinge 640.

For example, a proximal end portion 612 of the hinged portion 626 may be coupled to a proximal end portion 613 of the central portion 603 via the hinge 640. As such, the hinged portion 626 may form various angles with the central portion 603, thereby increasing or decreasing the size of the slot 601.

The central portion 603 may be a first portion of a cylindrical structure, and the hinged portion 626 may be a second portion of the cylindrical structure. The central portion 603 and the hinged portion 626 may be hemisphere structures. In some examples, the central portion 603 may have a first flat portion 615 (e.g., edges of the hemisphere structure), and the hinged portion 626 may have a second flat portion 614 (e.g., edges of the hemisphere structure). The first flat portion 615 of the central portion 603 may be configured to engage the second flat portion 614 of the hinged portion 626.

In some examples, the central portion 603 may include at least one protrusion, non-smooth element, and/or teeth, to assist in gripping the implant. In some examples, the hinged portion 626 may include at least one protrusion, non-smooth element, and/or teeth, to assist in gripping the implant. In other examples, both the central portion 603 and the hinged portion 626 include at least one protrusion, non-smooth element, and/or teeth to assist in gripping the implant.

A portion of the implant (e.g., implant 130) may be disposed within the slot 601. Then, as shown in FIG. 6B, the hinged portion 626 may be moved closer to the central portion 603, thereby securing the portion of the implant between the hinged portion 626 and the central portion 603. Then, the operator may rotate the handle 622 to wind the implant around the central portion 603 and the hinged portion 626. Referring to FIG. 6A, the sheath 604 and/or the elongated shaft 602 may be in the open position. In this position, the hinged portion 626 may be disposed in a position away from the central portion 603 (e.g., due to gravity). Referring to FIG. 6B, the sheath 604 and/or the elongated shaft 602 may be moved to the closed position along the axis A2, thereby engaging and pushing the hinged portion 626 closer to the central portion 603. In the closed position, the sheath 604 may be configured to enclose the implant. Also, the sheath 604 may be configured to enclose the hinged portion 626, the central portion 603, and the hinge 640.

Figure 7:
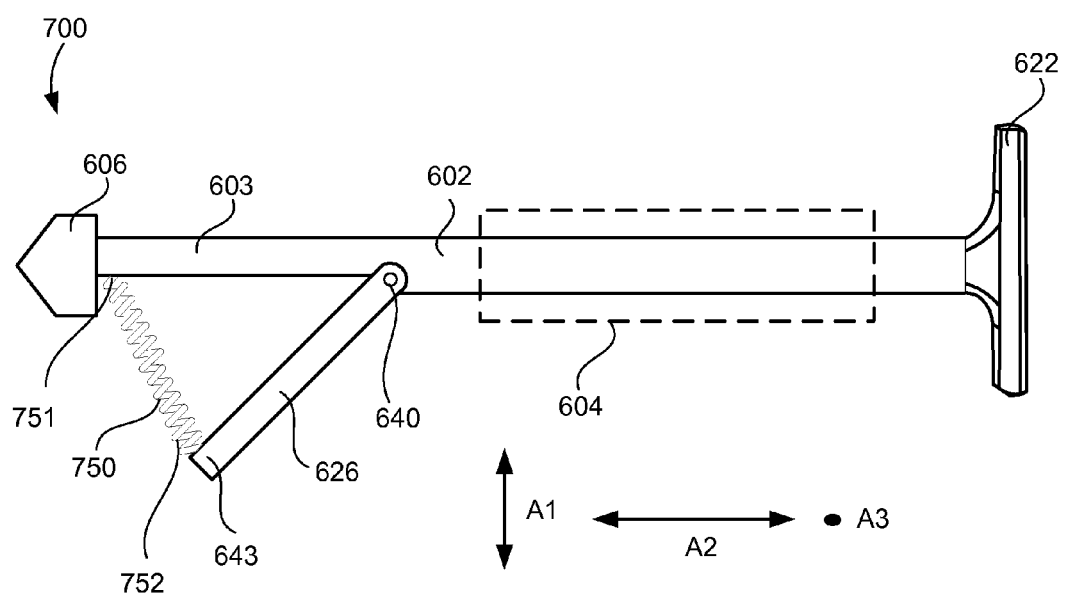
FIG. 7 illustrates a medical device according to another aspect.

FIG. 7 illustrates a medical device 700 according to another aspect. The medical device 700 is the same as the medical device 600 of FIGS. 6A and 6B except that a compression spring 750 is connected to the central portion 603 and the hinged portion 626. For example, a first end portion 751 of the compression spring 750 may be coupled to the central portion 603 at a location proximate to the cap 606, and a second end portion 752 of the compression spring 750 may be coupled to the distal end portion 643 of the hinged portion 626. In some examples, the compression spring 750 is biased to the closed position as shown in FIG. 6B. In other examples, the compression spring 750 is biased to the open position as shown in FIG. 6A.

Figure 8:
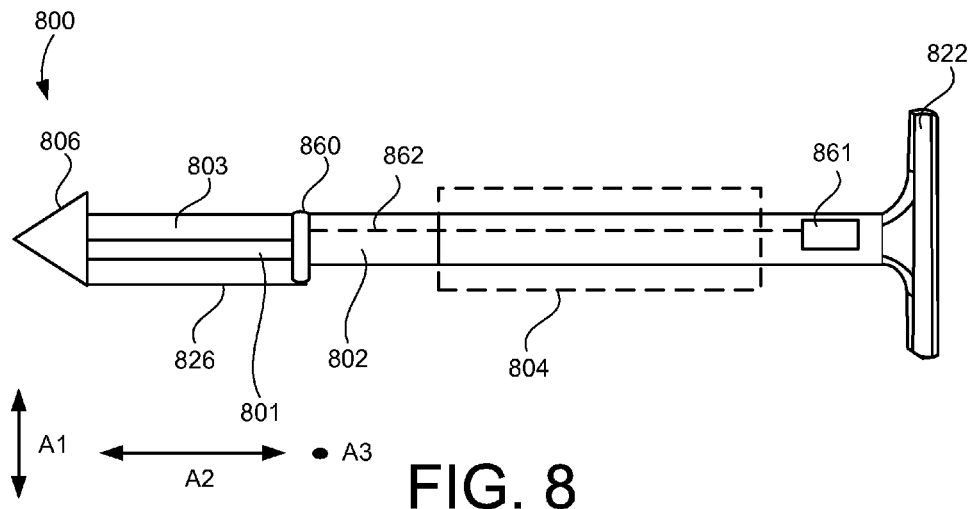
FIG. 8 illustrates a medical device according to another aspect.

FIG. 8 illustrates a medical device 800 according to another aspect. The medical device 800 includes a cap 806, an elongated shaft 802, a handle 822 connected to the elongated shaft 802, and a sheath 804 disposed around a portion of the elongated shaft 802. In some examples, the cap 806 may be the distal end portion 106/206 of FIGS. 1-5, the handle 822 may be the handle 122/222 of FIGS. 1-5, the sheath 804 may be the sheath 104/204 of FIGS. 1-5, and the elongated shaft 802 may be the elongated shaft 102/202 of FIGS. 1-5. Because these components were previously described, the differences between the medical device 800 and the previous aspects will be discussed below. Also, the medical device 800 may include one or more stopping members 128/228 in order to limit the movement of the elongated shaft 802 in relation to the sheath 804.

In this aspect, the elongated shaft 802 is split into a first shaft portion 803 and a second shaft portion 826 similar to the description of FIGS. 6A-6B. The first shaft portion 803 may be coupled to the cap 806. The first shaft portion 803 is an extension of the elongated shaft 802. In other examples, the first shaft portion 803 is a separate component from the elongated shaft 802, and coupled to the elongated shaft 802.

The second shaft portion 826 may be moveably coupled to the first shaft portion 803 via a connection member 860 such that a size of a slot 801 may be increased or decreased. The slot 801 may be configured to receive a portion of the implant (e.g., implant 130). The first shaft portion 803 and the second shaft portion 826 may be connected to the connection member 860 in a manner that allows the second shaft portion 826 to be moved closer or further away from the first shaft portion 803 along the axis A1. The second shaft portion 826 may be moved to various distances away from the first shaft portion 803 may manipulating the connection member 860.

The connection member 860 may be a threaded elongated member with the first shaft portion 803 and the second shaft portion 826 connected to the threaded member in a manner similar to a wrench. For example, rotation of the threaded member may cause the second shaft portion 826 to be moved closer or further away from the first shaft portion 803, thereby increasing or decreasing the slot 801.

Also, the connection member 860 may be connected to an actuation member 862 configured to control the operation of the connection member 860. In some examples, the actuation member 862 may be a wire, suture, or any type of elongated material. The actuation member 862 may be configured to control the connection member 860, thereby moving the second shaft portion 826. The operation of the actuation member 862 includes pulling the actuation member 862. In some examples, the connection member 860 may be spring-loaded to return to the original position (e.g., closed or open) when the actuation member 862 is no longer being pulled. Also, the actuation member 862 may be coupled to a trigger 861. The trigger may be disposed on the elongated shaft 802 or on the handle 822. The trigger 861 may be operated to pull the actuation member 862 thereby rotating the connection member 860.

Figure 9:
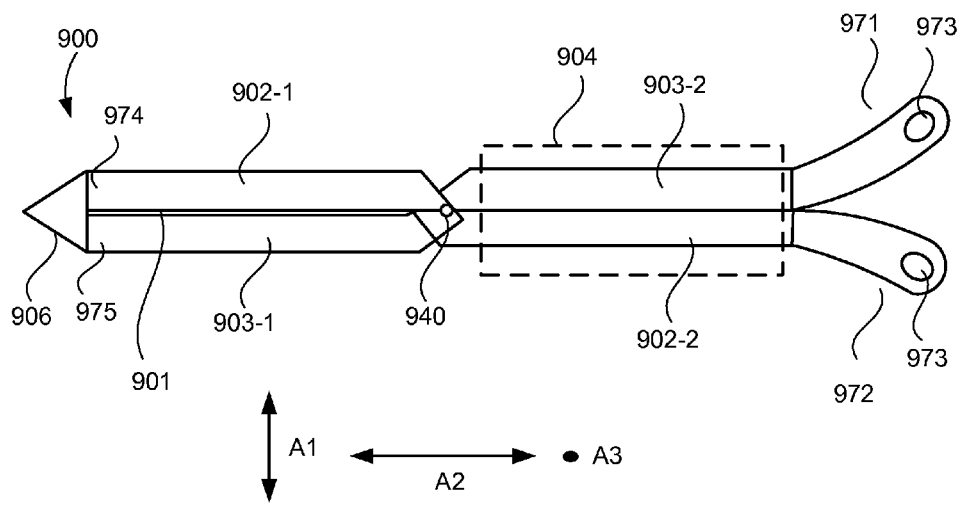
FIG. 9 illustrates a medical device according to another aspect.

FIG. 9 illustrates a medical device 900 according to another aspect. The medical device 900 of FIG. 9 splits the elongated shaft 102/202 into a first shaft 902 and a second shaft 903. The first shaft 902 is coupled to the second shaft 903 via a hinge 940 such that the first shaft 902 and the second shaft 903 operate similar to scissors. Also, the medical device 900 may include a cap 906 and a sheath 904. In some examples, the cap 906 may be the distal end portion 106/206 of FIGS. 1-5, and the sheath 904 may be the sheath 104/204 of FIGS. 1-5. Because these components were previously described, the differences between the medical device 900 and the previous aspects will be discussed below. Also, the medical device 900 may include one or more stopping members 128/228 in order to limit the movement of the first and second shafts 902, 903 in relation to the sheath 904.

The first shaft 902 may include an distal end portion 974 coupled to the cap 906, and a proximal end portion 972 forming a handle configured to be grasp by an operator. The second shaft 903 may include a distal end portion 975 and a proximal end portion 971 forming a handle configured to be grasped by an operator. In this example, the distal end portion 975 is not coupled to the cap 906. Alternatively, the distal end portion 975 of the second shaft 903 is coupled to the cap 906 while the distal end portion 974 is not coupled to the cap 906.

The first shaft 902 may include a first shaft portion 902-1 disposed between the cap 906 and the hinge 940, and a second shaft portion 902-2 disposed between the proximal end portion 972 and the hinge 940. The second shaft 903 may include a first shaft portion 903-1 disposed between the cap 906 and the hinge 940, and a second shaft portion 902-2 disposed between the proximal end portion 971 and the hinge 940. The first shaft portion 902-1 of the first shaft 902 may be disposed on top of the first shaft portion 903-1 of the second shaft 903, and the second shaft portion 902-2 of the first shaft 902 may be disposed on the bottom of the second shaft portion 903-2 of the second shaft 903 (or vice versa).

The proximal end portion 972 of the first shaft 902 may include a curved portion that extends away from the first shaft 902. The proximal end portion 971 of the second shaft 903 may include a curved portion that extends away from the second shaft 903. Also, each of the proximal end portion 971 and the proximal end portion 972 may define an opening 973 such that two fingers of the operator may be received within the openings 973.

When the proximal end portion 971 is further spaced apart from the proximal end portion 972, the first shaft portion 902-1 of the first shaft 902 moves away from the first shaft portion 903-1 of the second shaft 903, thereby creating a slot 901 configured to receive a portion of an implant. Then, the proximal end portion 971 is moved closer to the proximal end portion 972, thereby closing the opening to secure the implant. Then, the implant may be wrapped around the first shaft 902 and the second shaft 903 by rotating the first shaft 902 and the second shaft 903.

Figure 10A:
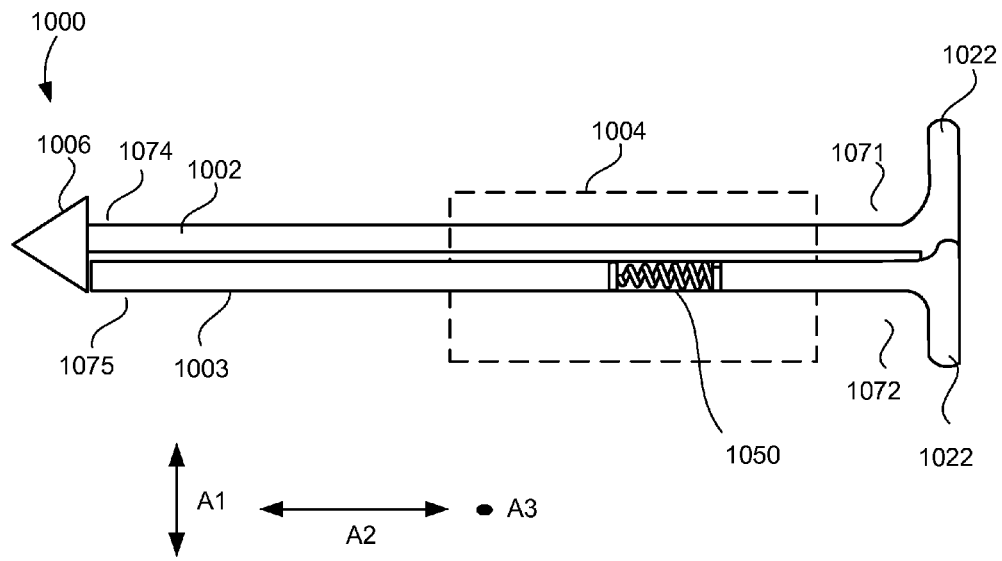
FIG. 10A illustrates a medical device in a first configuration according to another aspect.
Figure 10B:
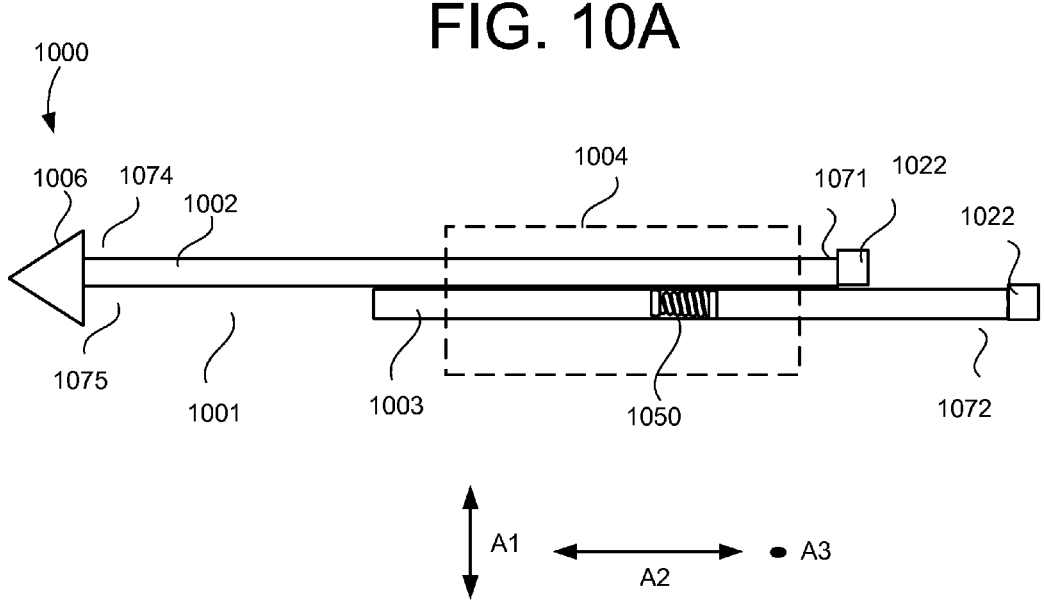
FIG. 10B illustrates a medical device of FIG. 10A in a second configuration according to an aspect.

FIGS. 10A-10B illustrates perspectives of a medical device 1000 according to another aspect. The medical device 1000 of FIG. 10 splits the elongated shaft into a first shaft 1002 and a second shaft 1003. The second shaft 1003 may move from a first position (e.g., FIG. 10A) to a second position (e.g., FIG. 10B) along the axis A2. In one example, the second shaft 1003 is proximally moved along the axis A2 until reaching the second position, thereby creating a slot 1001. For example, the slot 1001 may be a non-overlapping portion (e.g., the first shaft 1002 and the second shaft 1003 do not overlap). Then, a portion of the implant may be placed within the slot 1001, and the second shaft 1003 may be moved back to the first position shown in FIG. 10A, thereby securing the implant to the medical device 1000. Then, the implant may be wrapped around the first shaft 1002 and the second shaft 1003 by rotating the first shaft 1002 and the second shaft 1003.

The medical device 1000 may include a cap 1006, a sheath 1004, and a handle 1022 on each shaft. In some examples, the cap 1006 may be the distal end portion 106/206 of FIGS. 1-5, the sheath 1004 may be the sheath 104/204 of FIGS. 1-5, and the handle 1022 may be the handle 122/222 of FIGS. 1-5. Because these components were previously described, the differences between the medical device 1000 and the previous aspects will be discussed below. Also, the medical device 1000 may include one or more stopping members 128/228 in order to limit the movement of the first and second shafts 1002, 1003 in relation to the sheath 1004.

The first shaft 1002 may include a distal end portion 1074 coupled to the cap 1006 and a proximal end portion 1071 coupled to the handle 1022 of the first shaft 1002. The second shaft 1003 may include a distal end portion 1075 and a proximal end portion 1072 coupled to the handle 1022 of the second shaft 1003. In this example, the distal end portion 1075 of the second shaft 1003 is not coupled to the cap 1006. Alternatively, the distal end portion 1075 of the second shaft 1003 is coupled to the cap 1006, and the distal end portion 1074 of the first shaft 1002 is not coupled to the cap 1006. The second shaft 1003 may move along the axis A2 by applying a force to the handle 1022 of the second shaft 1003. Also, the second shaft 1003 may be associated with a biasing mechanism 1050 configured to bias the second shaft 1003 in the first position or the second position. In some examples, the biasing mechanism 1050 may be a compression spring.

Figure 11:
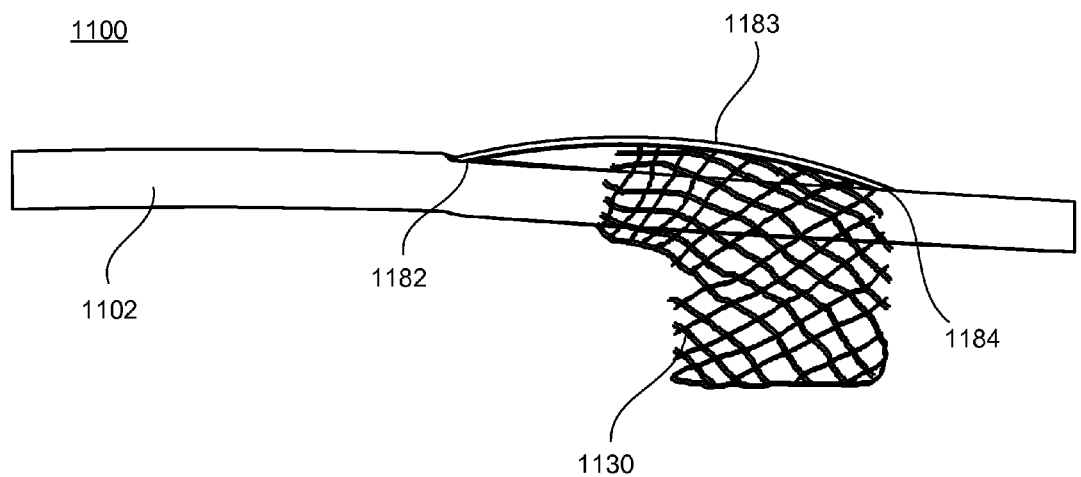
FIG. 11 illustrates a medical device according to another aspect.

FIG. 11 illustrates a portion of a medical device 1100 according to an aspect. The medical device 1100 may include an elongated shaft 1102, and an implant 1130 coupled to the elongated shaft 1102. Also, the medical device 1100 of FIG. 11 may include a flexible connection member 1183 coupled to the elongated shaft 1102. The elongated shaft 1102 and the flexible connection member 1183 may be used in conjunction with any of the medical devices described herein. In some examples, the flexible connection member 1183 may be a wire. The flexible connection member 1183 may be configured to flex or bend away from the elongated shaft 1102 and/or flex or bend towards the elongated shaft 1102. The implant 1130 may be disposed between the flexible connection member 1183 and the elongated shaft 1102, thereby securing the implant 1130 to the elongated shaft 1102. In this aspect, the elongated shaft 1102 may define an internal lumen. The elongated shaft 1102 may define a first opening 1182 to the internal lumen and a second opening 1184 to the internal lumen. The second opening 1184 may be disposed on the elongated shaft 1102 at a distance from the first opening 1182 such that the implant 1130 may be wrapped around a portion of the elongated shaft 1102 between the first opening 1182 and the second opening 1184.

The flexible connection member 1183 may be inserted into the first opening 1182 and the second opening 1184 such that the flexible connection member 1183 extends over the portion of the elongated shaft 1102 between the first opening 1182 and the second opening 1184. A first end portion (e.g., distal end portion) of the flexible connection member 1183 may be fixably coupled to the elongated shaft 1102 or another portion of the medical device, and a second end portion (e.g., proximal end portion) of the flexible connection member 1183 may extend through the elongated shaft 1102 and be connected to an activation member (e.g., trigger, pusher, etc.). Operation of the activation member may pull the flexible connection member 1183 closer to the elongated shaft 1102.

Figure 12:
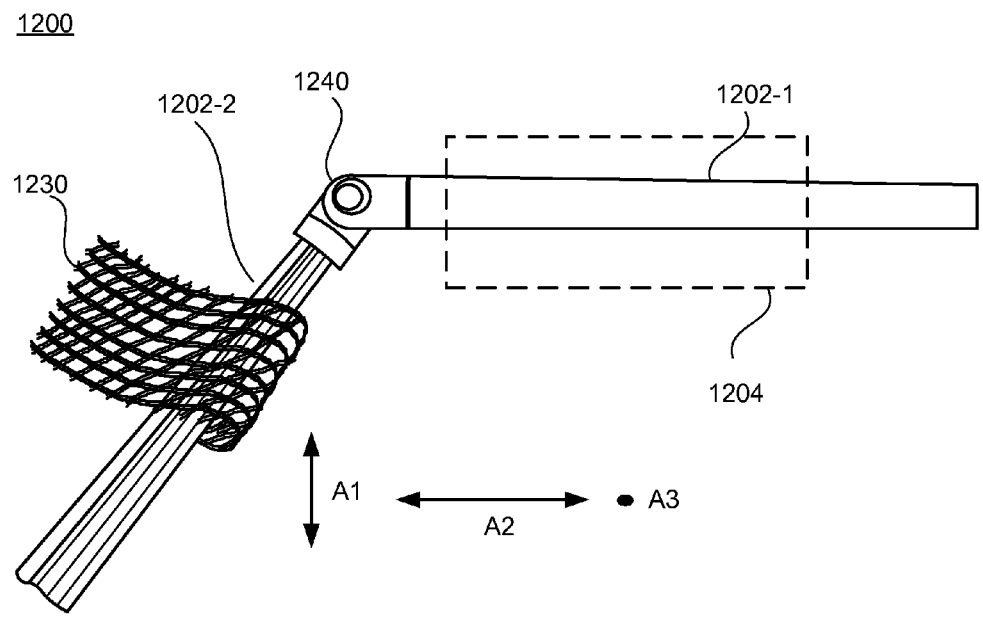
FIG. 12 illustrates a medical device according to another aspect.

FIG. 12 illustrates a portion of a medical device 1200 having an elongated shaft 1202 according to another aspect. The shaft 1202 of FIG. 12 may be used in conjunction with any of the medical devices described herein. In this example, the elongated shaft 1202 may include a first shaft portion 1202-1 coupled to a second shaft portion 1202-2 via a hinge 1240. Also, the medical device 1200 may include a sheath 1204 disposed around a portion of the elongated shaft 1202. The second shaft portion 1202-2 may be configured to retain an implant 1230 in any of the manners previously described. The hinge 1240 may be disposed within a middle portion of the elongated shaft 1202 such that the second shaft portion 1202-2 may be movable in any direction. For example, the first shaft portion 1202-1 may be configured to rotate about its central axis, and the second shaft portion 1202-2 may be configured to move with respect to the first shaft portion 1202-1 via the hinge 1240. Although not shown in FIG. 12, the second shaft portion 1202-2 may be coupled to any of the distal end portions previously described.

Also, the second shaft portion 1202-2 may be configured to rotate about its central axis. In this manner, the rotation of the second shaft portion 1202-2 may assist in unrolling the implant 1230 from the second shaft portion 1202-2. The second shaft portion 1202-2 may be coupled to an activation member configured to automatically rotate the second shaft portion 1202-2. The hinge 1240 may be connected to an activation member in order to allow the user to control the angle of the second shaft portion 1202-2 with respect to the first shaft portion 1202-1. The sheath 1204 may include a flexible, bendable material that can be bent when the second shaft portion 1202-2 is angled with respect to the first shaft portion 1202-1.

Figure 13:
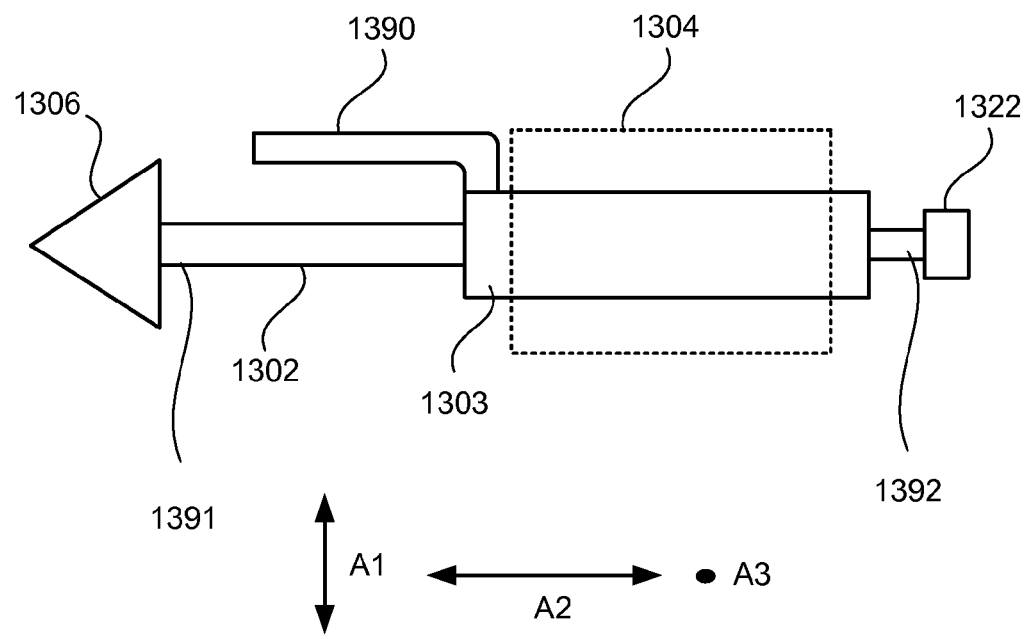
FIG. 13 illustrates a medical device according to another aspect.

FIG. 13 illustrates a medical device 1300 according to another aspect. The medical device 1300 may include a first elongated shaft 1302 disposed within a portion of a second elongated shaft 1303. The distal end portion 1391 of the first elongated shaft 1302 may be coupled a cap 1306 and the proximal end portion 1392 of the first elongated shaft 1302 may be coupled to a handle 1322. In some examples, the cap 1306 may be the distal end portion 106/206 of FIGS. 1-5, the sheath 1304 may be the sheath 104/204 of FIGS. 1-5, and the handle 1322 may be the handle 122/222 of FIGS. 1-5. Because these components were previously described, the differences between the medical device 1300 and the previous aspects will be discussed below. Also, the medical device 1300 may include one or more stopping members 128/228 in order to limit the movement of the first and/or second elongated shaft 1302, 1303 in relation to the sheath 1304 and/or one of the first elongated shaft 1302 and the second elongated shaft 1303.

The first elongated shaft 1302 may be considered an inner rod that may slide and rotate within the second elongated shaft 1303. In some examples, the second elongated shaft 1303 may be shorter than the first elongated shaft 1302. A protrusion 1390 may extend from the second elongated shaft 1303 and may extend in a direction parallel with the first elongated shaft 1302. When the first elongated shaft 1302 is rotated, the protrusion 1390 may engage an implant coupled to the second elongated shaft 1303 in order to assist in the wrapping of the implant around the second elongated shaft 1303. The sheath 1304 may be configured to move in a direction parallel with the first elongated shaft 1302 or the second elongated shaft 1303. For example, the sheath 1304 may move in a distal direction such that sheath 1304 may cover and protect the implant which is coupled to the first elongated shaft 1302.

Alternatively, instead of using two shafts, the medical device may use a single elongated shaft (e.g., the first elongated shaft 1302). In this aspect, the protrusion 1390 may be coupled through a ring fixed onto the first elongated shaft 1302 such that the first elongated shaft 1302 may rotate while keeping the protrusion 1390 relatively fixed. In another alternative aspect, the protrusion 1390 may be connected to the cap 1306 and extend towards the handle 1322.

Figure 14:
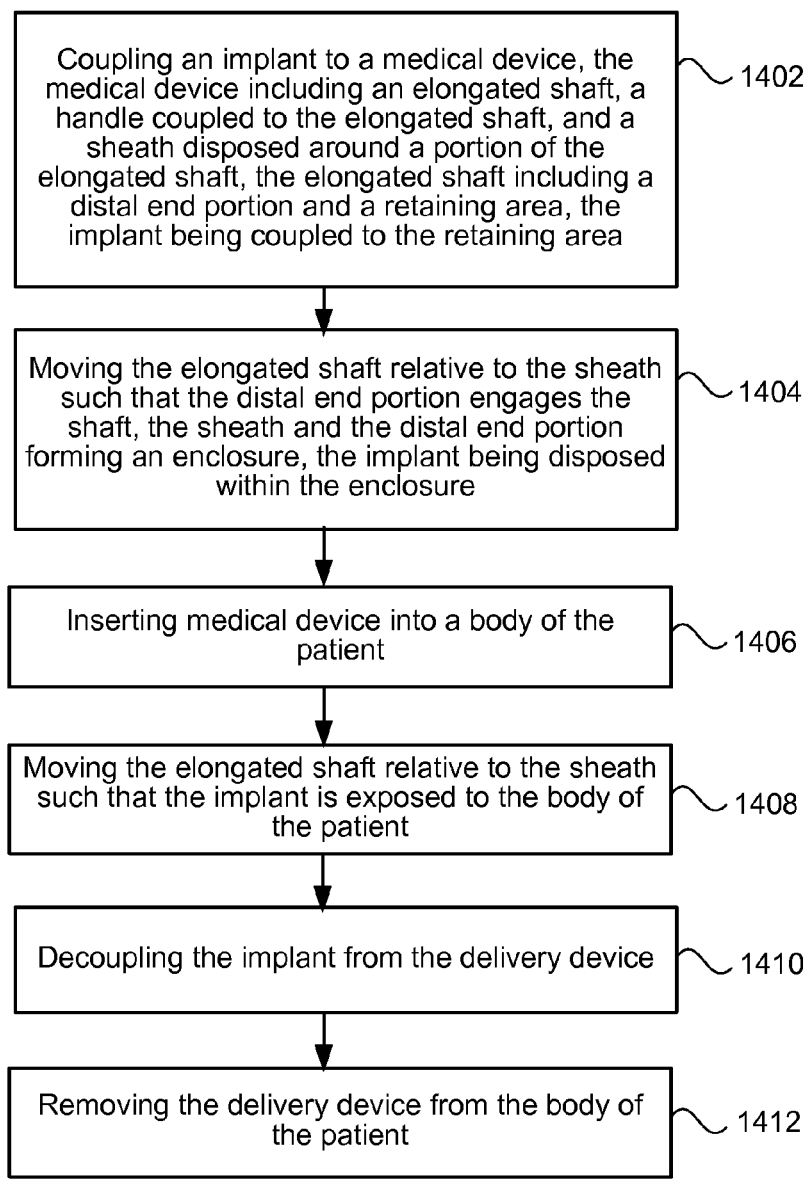
FIG. 14 illustrates a flow chart for a method of inserting a medical device into a body of the patient according to an aspect.

FIG. 14 is a flow chart for a method 1400 of inserting a medical device into a body of the patient according to an aspect. The method 1400 may be applied to any type of surgical procedure that delivers an implant into the body. In some examples, the surgical procedure may be a sacrocolpopexy. The sacrocolpopexy procedure may be performed using an open abdominal technique or with the use of minimally invasive surgery, such as laparoscopy or robotic-assisted surgery. The method 1400 may ensure that the implant is protected during introduction into the body. Also, the method 1400 may facilitate the coupling of the implant in a rolled configuration before the medical device is inserted into the body and the de-coupling of the implant from the rolled configuration while the medical device is in the body.

In 1402, an implant may be coupled to a medical device. The implant may be the implant 130 of FIGS. 1 and 2. The medical device may include any of the medical devices described herein. The medical device may include an elongated shaft (or cap), a handle coupled to the elongated shaft, and a sheath disposed around a portion of the elongated shaft. The elongated shaft including a distal end portion and a retaining area. The implant is coupled to the retaining area. For example, a portion of the implant may be placed on a surface of the retaining area, and the elongated shaft may be rotated (e.g., in conjunction with the handle) in order to wind the implant around the retaining area. If the retaining area defines a slot (e.g., any of the slots described in the figures), the portion of the implant may be inserted into the slot, and the elongated shaft may be rotated, thereby winding the implant around the elongated shaft at the retaining area.

In 1404, the elongated shaft may be moved relative to the sheath such that the distal end portion engages the shaft, where the sheath and the distal end portion form an enclosure such that the implant is disposed within the enclosure. In some examples, the implant may be fully enclosed, thereby protecting the implant when the medical device is inserted into the body. In some examples, the enclosure may be fluid-tight.

In 1406, the medical device may be inserted into the body of the patient. For example, the medical device may be delivered to a location within the body of the patient.

In 1408, the elongated shaft may be moved relative to the sheath such that the implant is exposed to the body of the patient. For example, the sheath may be slide in the other direction, thereby exposing the implant.

In 1410, the implant may be decoupled from the medical device. For example, the elongated shaft (in conjunction with the handle) may be rotated such that the implant is unwound from the elongated shaft. Also, a surgical tool may be used to grip a portion of the implant to assist in the unwinding.

In 1412, the medical device may be removed from the body of the patient.

According to an aspect, a medical device may include an elongated shaft having a longitudinal axis. The elongated shaft may be configured to rotate about the longitudinal axis. The elongated shaft may include a retaining area configured to couple an implant such that the implant is wound around the elongated shaft at the retaining area. The medical device may also include a sheath disposed around a portion of the elongated shaft. The elongated shaft may be configured to move in relation to the sheath. The elongated shaft may be configured to move in a direction parallel to the longitudinal axis between a first position and a second position. When the elongated shaft is in the first position, the retaining area is disposed outside of a cavity defined by the sheath. When the elongated shaft is in the second position, the retaining area is disposed within the cavity defined by the sheath.

The retaining area may include a slot, where the slot is configured to receive a portion of the implant. The slot may define an opening on a surface of the elongated shaft at the retaining area. The slot may include a first edge and a second edge such that the portion of the implant is received between the first edge and the second edge. The retaining area may include at least one protrusion on a surface of the elongated shaft. The elongated shaft may include a distal end portion, where the distal end portion engages the sheath when the elongated shaft is in the second position such that the cavity of the sheath and the distal end portion enclose the retaining area. The distal end portion of the elongated shaft may include a tissue piercing portion configured to pierce bodily tissue when inserted into a body of a patient. The tissue piercing portion may be blunt. The medical device may include at least one stopper member disposed on a portion of the elongated shaft, where the at least one stopper member configured to substantially prevent movement in at least one direction of the elongated shaft. The stopper member may include a ring disposed around the portion of the elongated shaft. The sheath may include a protective portion and an extension portion. The retaining area is disposed within a cavity defined by the protective portion when the elongated shaft is in the second position. The protective portion may have a size larger than the extension portion. The distal end portion of the elongated shaft may include an inner diameter portion and an outer diameter portion, where the inner diameter portion is disposed within a portion of the sheath such that inner diameter portion forms a cap closing an opening of the cavity of the sheath.

According to an aspect, a method for delivering an implant may include coupling an implant to a delivery device. The delivery device may include an elongated shaft and a sheath disposed around a portion of the elongated shaft, where the sheath defines a cavity. The elongated shaft may include a distal end portion and a retaining area, where the implant is coupled to the retaining area. The method may include moving the elongated shaft relative to the sheath such that distal end portion engages the sheath, where the cavity of the sheath and the distal end portion form an enclosure and the implant is disposed within the enclosure.

The retaining area may define a slot, and the coupling the implant to the delivery device includes inserting a portion of the implant into the slot and rotating the elongated shaft such that the implant is wound around a surface of the retaining area. The method may further include moving the elongated shaft relative to the sheath such that the implant is outside the cavity defined by the sheath and decoupling the implant from the delivery device. The decoupling the implant from the delivery device may include rotating the elongated shaft such that the implant is unwound from the retaining area.

According to an aspect, the medical device may include an elongated shaft having a longitudinal axis. The elongated shaft may be configured to rotate about the longitudinal axis. The elongated shaft may include a retaining area configured to retain an implant in a rolled configuration such that the implant is wound around the elongated shaft at the retaining area. The medical device may include a sheath disposed around a portion of the elongated shaft. The elongated shaft is configured to move in relation to the sheath. The elongated shaft is configured to move in a direction parallel to the longitudinal axis between a first position and a second position. When the elongated shaft is in the first position, the retaining area is disposed outside of a cavity defined by the sheath. When the elongated shaft is in the second position, the retaining area is disposed within the cavity defined by the sheath.

The retaining area may include a slot, where the slot receives a portion of the implant. The retaining area may include at least one protrusion on a surface of the elongated shaft. The elongated shaft may include a distal end portion. The distal end portion is configured to engage the sheath when the elongated shaft is in the second position such that the cavity of the sheath and the distal end portion enclose the retaining area. The distal end portion may include a tissue piercing portion configured to pierce bodily tissue when inserted into a body of a patient. The medical device may include at least one stopper member disposed on a portion of the elongated shaft, the at least one stopper member configured to substantially prevent movement in at least one direction of the elongated shaft. The stopper member may include a ring disposed around the portion of the elongated shaft. The sheath may include a protective portion and an extension portion, where the retaining area is disposed within a cavity defined by the protective portion when the elongated shaft is in the second position. The protective portion may have a size larger than the extension portion.

According to an aspect, a medical package may include an implant and an elongated shaft having a longitudinal axis, where the elongated shaft is configured to rotate about the longitudinal axis. The elongated shaft may include a distal end portion and a proximal end portion. The distal end portion may include a tissue piercing portion. The elongated shaft may include a retaining area disposed between the distal end portion and the proximal end portion, where the retaining area is configured to retain the implant. The medical package may further include a sheath disposed around a portion of the elongated shaft, the elongated shaft configured to move in relation to the sheath. The elongated shaft is configured to move in a direction parallel to the longitudinal axis between a first position and a second position. When the elongated shaft is in the first position, the retaining area is disposed outside a cavity defined by the sheath. When the elongated shaft is in the second position, the distal end portion engages the sheath such that the implant is enclosed by the distal end portion and the cavity of the sheath.

The distal end portion may include an inner diameter portion and an outer diameter portion, where the inner diameter portion is disposed within a portion of the sheath such that inner diameter portion forms a cap closing an opening of the cavity of the sheath. The sheath may include a protective portion and an extension portion, where the protective portion is configured to be engaged with the distal end portion of the elongated shaft, and the extension portion has a shape smaller than a shape of the protective portion. The retaining area may define a slot configured to receive a portion of the implant. The slot may define an opening on a surface of the elongated shaft at the retaining area. The slot may include a first edge and a second edge such that the portion of the implant is received between the first edge and the second edge. The tissue piercing portion may be blunt. The medical package may include a first stopper member configured to substantially prevent movement of the elongated shaft beyond the first position in a first direction, and a second stopper member configured to substantially prevent movement of the elongated shaft beyond the second position in a second direction. At least one of the first stopper member and the second stopper member may include a ring disposed around the portion of the elongated shaft.

According to an aspect, a method for inserting a delivery device into a body of a patient may include coupling an implant to a delivery device. The delivery device may include an elongated shaft and a sheath disposed around a portion of the elongated shaft. The sheath may define a cavity. The elongated shaft may include a distal end portion and a retaining area, where the implant is coupled to the retaining area. The method may further include moving the elongated shaft relative to the sheath such that distal end portion engages the sheath, and the cavity of the sheath and the distal end portion form an enclosure such that the implant is disposed within the enclosure. The method may further include insert the delivery device into a body of the patient.

The retaining area may define a slot, and the coupling the implant to the delivery device includes inserting a portion of the implant into the slot and rotating the elongated shaft such that the implant is wound around a surface of the retaining area. The method may further include moving the elongated shaft relative to the sheath such that the implant is outside the cavity defined by the sheath, decoupling the implant from the delivery device, and removing the delivery device from the body of the patient. The decoupling the implant from the delivery device may include rotating the elongated shaft such that the implant is unwound from the retaining area.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
   an elongated shaft having a longitudinal axis, the elongated shaft including a distal end portion, a proximal end portion, and a shaft portion disposed between the distal end portion and the proximal end portion, the proximal end portion including a handle, the elongated shaft configured to rotate about the longitudinal axis, the elongated shaft including a retaining area disposed on the shaft portion, the retaining area configured to retain an implant in a rolled configuration such that the implant is wound around the shaft portion at the retaining area;
   a sheath disposed around a portion of the shaft portion of the elongated shaft, the elongated shaft configured to move in relation to the sheath, the elongated shaft configured to move in a direction parallel to the longitudinal axis between a first position and a second position, wherein when the elongated shaft is in the first position, the retaining area is disposed outside of a cavity defined by the sheath such that the implant is not covered by the sheath, wherein when the elongated shaft is in the second position, the retaining area is disposed within the cavity defined by the sheath such that the implant is covered by the sheath;
   a first stopper member configured to substantially prevent movement of the elongated shaft beyond the first position in a first direction; and
   a second stopper member configured to substantially prevent movement of the elongated shaft beyond the second position in a second direction.

2. The medical device of claim 1, wherein the retaining area includes a slot defined by the shaft portion adjacent to the distal end portion, the slot configured to receive an edge portion of the implant.

3. The medical device of claim 1, wherein the retaining area includes at least one protrusion on a surface of the elongated shaft.

4. The medical device of claim 1, wherein the distal end portion is configured to contact the sheath when the elongated shaft is in the second position such that the sheath and the distal end portion enclose the retaining area and the implant.

5. The medical device of claim 1, wherein the distal end portion includes a tissue piercing portion configured to pierce bodily tissue when inserted into a body of a patient.

6. The medical device of claim 1, wherein the first stopper member includes a first ring disposed around a first portion of the elongated shaft, and the second stopper member includes a second ring disposed around a second portion of the elongated shaft.

7. The medical device of claim 1, wherein the sheath includes a protective portion and an extension portion, the retaining area being disposed within a cavity defined by the protective portion when the elongated shaft is in the second position, the protective portion having an outer diameter larger than an outer diameter of the extension portion.

8. A medical package comprising:
   an implant;
   an elongated shaft having a longitudinal axis, the elongated shaft configured to rotate about the longitudinal axis, the elongated shaft including a distal end portion and a proximal end portion, the distal end portion including a tissue piercing portion, the elongated shaft including a retaining area disposed between the distal end portion and the proximal end portion, the retaining area configured to retain the implant;
   a sheath disposed around a portion of the elongated shaft, the elongated shaft configured to move in relation to the sheath, the elongated shaft configured to move in a direction parallel to the longitudinal axis between a first position and a second position, wherein when the elongated shaft is in the first position, the retaining area is disposed outside a cavity defined by the sheath, wherein when the elongated shaft is in the second position, the distal end portion engages the sheath such that the implant is enclosed by the distal end portion and the cavity of the sheath;
   a first stopper member disposed on a first portion of the elongated shaft, the first stopper member configured to substantially prevent movement of the elongated shaft beyond the first position in a first direction; and
   a second stopper member disposed on a second portion of the elongated shaft, the second stopper member configured to substantially prevent movement of the elongated shaft beyond the second position in a second direction.

9. The medical package of claim 8, wherein the distal end portion includes an inner diameter portion and an outer diameter portion, the inner diameter portion being disposed within a portion of the sheath such that inner diameter portion forms a cap closing an opening of the cavity of the sheath.

10. The medical package of claim 8, wherein the sheath includes a protective portion and an extension portion, the protective portion configured to be engaged with the distal end portion of the elongated shaft, the extension portion having an outer diameter smaller than an outer diameter of the protective portion.

11. The medical package of claim 8, wherein the retaining area defines a slot configured to receive an edge of the implant.

12. The medical package of claim 11, wherein the slot defines an opening on a surface of the elongated shaft at the retaining area, the slot including a first edge and a second edge such that the portion of the implant is received between the first edge and the second edge.

13. The medical package of claim 8, wherein the tissue piercing portion is blunt.

14. The medical package of claim 8, wherein the first stopper member includes a first ring disposed around the first portion of the elongated shaft, and the second stopper member includes a second ring disposed around the second portion of the elongated shaft.

15. A method for treating a pelvic organ prolapse, the method comprising:
- coupling an implant to a delivery device, the delivery device including an elongated shaft and a sheath disposed around a portion of the elongated shaft, the sheath defining a cavity, the elongated shaft including a distal end portion, a proximal end portion, and a shaft portion disposed between the distal end portion and the proximal end portion, the proximal end portion including a handle, the shaft portion defining a retaining area, the implant being coupled to the retaining area in a rolled configuration;
- moving the elongated shaft relative to the sheath such that distal end portion engages the sheath, the cavity of the sheath and the distal end portion forming an enclosure, the implant being disposed within the enclosure;
- inserting a portion of the delivery device into a pelvic region of the patient, the handle being disposed outside of a body of the patient;
- moving the elongated shaft relative to the sheath such that the implant is outside the cavity defined by the sheath while the portion of the delivery device is disposed within the body of the patient; and
- decoupling the implant from the delivery device by rotating the handle.

16. The method of claim 15, wherein the retaining area defines a slot, and the coupling the implant to the delivery device includes inserting a portion of the implant into the slot and winding the implant around the retaining area using the handle.

17. The method of claim 15 further comprising:
- removing the delivery device from the body of the patient.

* * * * *